United States Patent
Xu

(10) Patent No.: US 10,758,612 B2
(45) Date of Patent: Sep. 1, 2020

(54) ANTIBODIES TO TUMOR ASSOCIATED COMPLEX N-GLYCANS WITH TERMINAL GLCNACβ RESIDUES AND METHODS OF USE THEREOF

(71) Applicant: Washington University, St. Louis, MO (US)

(72) Inventor: Mai Xu, St. Louis, MO (US)

(*) Notice: Subject to any disclaimer, the term of this patent is extended or adjusted under 35 U.S.C. 154(b) by 206 days.

(21) Appl. No.: 15/744,658

(22) PCT Filed: Jul. 15, 2016

(86) PCT No.: PCT/US2016/042435
§ 371 (c)(1),
(2) Date: Jan. 12, 2018

(87) PCT Pub. No.: WO2017/011728
PCT Pub. Date: Jan. 19, 2017

(65) Prior Publication Data
US 2018/0193455 A1   Jul. 12, 2018

Related U.S. Application Data

(60) Provisional application No. 62/192,750, filed on Jul. 15, 2015.

(51) Int. Cl.
| A61K 39/395 | (2006.01) |
| G01N 33/574 | (2006.01) |
| C07K 16/30 | (2006.01) |
| C07H 5/06 | (2006.01) |
| C07K 16/28 | (2006.01) |

(52) U.S. Cl.
CPC ........ *A61K 39/3955* (2013.01); *A61K 39/395* (2013.01); *C07H 5/06* (2013.01); *C07K 16/2809* (2013.01); *C07K 16/2818* (2013.01); *C07K 16/2848* (2013.01); *C07K 16/30* (2013.01); *G01N 33/574* (2013.01); *C07K 2317/41* (2013.01); *C07K 2317/565* (2013.01); *C07K 2317/92* (2013.01); *G01N 2400/38* (2013.01)

(58) Field of Classification Search
CPC ............................ A61K 39/3955; A61K 39/395
USPC ......................................................... 435/7.23
See application file for complete search history.

(56) References Cited

U.S. PATENT DOCUMENTS

| 4,241,046 A | 12/1980 | Papahadjopoulous et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 2006/0014672 A1* | 1/2006 | Natunen ............ C07H 3/06 424/185.1 |
| 2007/0269372 A1 | 11/2007 | Gelber |
| 2009/0010924 A1 | 1/2009 | Wu et al. |
| 2010/0021478 A1 | 1/2010 | Demuth et al. |
| 2013/0101504 A1* | 4/2013 | Trieu ............ C07K 16/18 424/1.49 |
| 2014/0234318 A1 | 8/2014 | Natunen et al. |

FOREIGN PATENT DOCUMENTS

WO   2014011988 A2   1/2014

OTHER PUBLICATIONS

Chothia, C. et al., "Canonical Structures for the Hypervariable Regions of Immunoglobulins," J. Mol. Biol., 1987, pp. 901-917, vol. 196, Academic Press Limited.
Chothia, C. et al., "Conformations of immunoglobulin hypervariable regions," Nat., Dec. 1989, pp. 878-883, vol. 342, Nature Publishing Group.
Co, M. et al., "Humanized antibodies for antiviral therapy," PNAS, Apr. 1991, pp. 2869-2873, vol. 88.
International Search Report and Written Opinion dated Dec. 16, 2016 from International Patent Application No. PCT/US2016/042435; 13 pgs.
Kolb, H. et al., "Click Chemistry: Diverse Chemical Function from a Few Good Reactions," Angew. Chem. Int. Ed., 2001, pp. 2004-2021, vol. 40, Wiley-VCH.
UniProtKB Accession No. D2VZ17_NAEGR, Naegleria gruberi (Amoeba) Predicted protein, Mar. 2, 2010, 4 pgs.

* cited by examiner

*Primary Examiner* — Sean E Aeder
(74) *Attorney, Agent, or Firm* — Polsinelli PC

(57) ABSTRACT

The present disclosure relates to antibodies specific tumor associated complex N-glycans with terminal GlcNAcβ residues and methods for detecting a tumor in a subject. The present disclosure also relates to therapeutic antibodies specific for tumor associated complex N-glycans with terminal GlcNAcβ residues.

21 Claims, 14 Drawing Sheets
(14 of 14 Drawing Sheet(s) Filed in Color)
Specification includes a Sequence Listing.

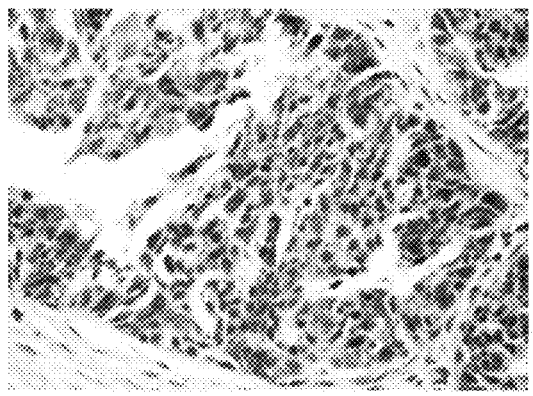
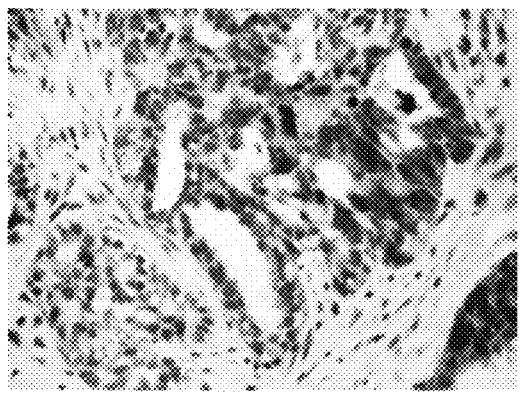
FIG. 10A  FIG. 10B
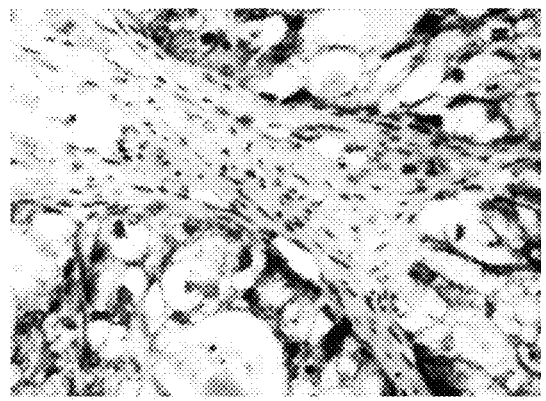
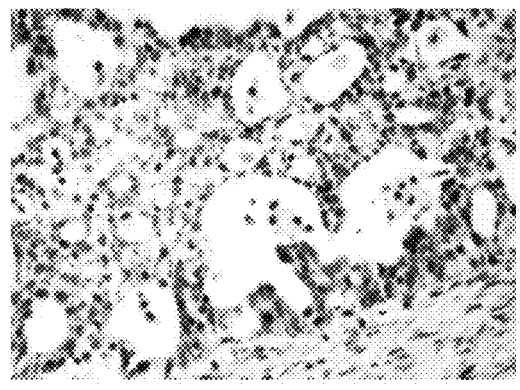
FIG. 10C  FIG. 10D
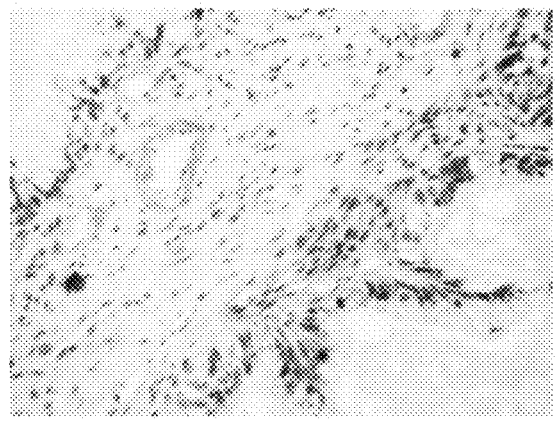
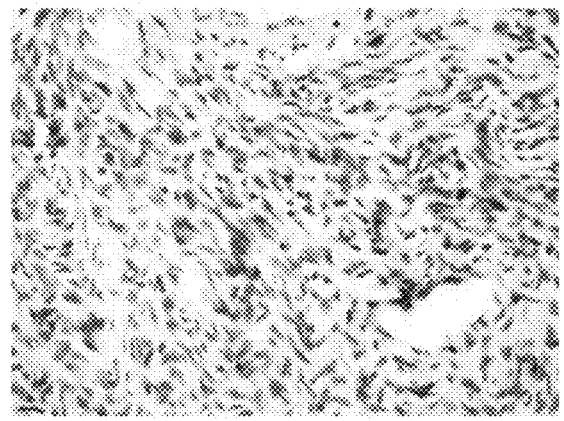
FIG. 10E  FIG. 10F

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 1

Ser Ala Ser Ser Ser Val Ser Tyr Met His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Glu Ile Ser Lys Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 3

Gln Gln Trp Asn Tyr Pro Leu Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: SYNTHESIZED
```

```
<400> SEQUENCE: 4

Gly Phe Thr Phe Ser Asp Tyr Gly Met Ala
1               5                   10

<210> SEQ ID NO 5
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 5

Phe Ile Ser Tyr Leu Ala Tyr Thr Val Phe Tyr Ala Asp Thr Val Thr
1               5                   10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 6

Glu Ala Tyr Gly Gly Gly Phe Thr Tyr
1               5

<210> SEQ ID NO 7
<211> LENGTH: 106
<212> TYPE: PRT
<213> ORGANISM: Artificial Sequence
<220> FEATURE:
<223> OTHER INFORMATION: SYNTHESIZED

<400> SEQUENCE: 7

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Tyr Thr
                85                  90                  95

Phe Gly Gly Gly Thr Lys Leu Glu Ile Lys
            100                 105

<210> SEQ ID NO 8
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 8

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30
```

Gly Met Ala Trp Val Arg Gln Ala Pro Gly Lys Gly Pro Glu Trp Val
          35                  40                  45

Ala Phe Ile Ser Tyr Leu Ala Tyr Thr Val Phe Tyr Ala Asp Thr Val
 50                  55                  60

Thr Gly Arg Phe Thr Ile Ser Arg Glu Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95

Ser Arg Glu Ala Tyr Gly Gly Gly Phe Thr Tyr Trp Gly Gln Gly Thr
            100                 105                 110

Leu Val Thr Val
         115

<210> SEQ ID NO 9
<211> LENGTH: 318
<212> TYPE: DNA
<213> ORGANISM: Artificial Sequence
<220> FEATURE:
<223> OTHER INFORMATION: SYNTHESIZED

<400> SEQUENCE: 9
gaaattgtgc tcactcagtc tccagccatc acagctgcat ctctgggggca aaaggtcacc      60 atcacctgca gtgccagctc aagtgtaagt tacatgcact ggtaccagca gaagtcaggc     120
acctccccca aaccatggat ttatgaaata tccaaactgg cttctggagt cccagctcgc     180
ttcagtggca gtgggtctgg gacctcttac tctctcacaa tcagcagcat ggaggctgaa     240
gatgctgcca tttattactg ccagcagtgg aattatcctc tgtacacgtt cggagggggg     300
accaagctgg aaataaaa                                                    318

<210> SEQ ID NO 10
<211> LENGTH: 348
<212> TYPE: DNA
<213> ORGANISM: Artificial Sequence
<220> FEATURE:
<223> OTHER INFORMATION: SYNTHESIZED

<400> SEQUENCE: 10
gaggtgaagt tggtggagtc tgggggaggc ttagtgcagc ctggagggtc ccggaaactc      60
tcctgtgcag cctctggatt cactttcagt gactacggaa tggcgtgggt tcgacaggct     120
ccagggaagg ggcctgagtg ggttgcattc attagttatt tggcatatac tgtcttctat     180
gcagacactg tgacgggccg attcaccatc tctagagaga tgccaaaaa cacccctgtac     240 ctggaaatga gcagtctgag gtctgaggac acagccatgt actactgttc aagggaggcg     300
tacgggggag ggtttactta ctggggccaa gggactctgg tcactgtc                  348

<210> SEQ ID NO 11
<211> LENGTH: 1386
<212> TYPE: DNA
<213> ORGANISM: Artificial Sequence
<220> FEATURE:
<223> OTHER INFORMATION: SYNTHESIZED

<400> SEQUENCE: 11
atggacttca ggctcagctt acttattttt gtccttattt taaaaggtgt ccagtgtgag      60
gtgaagttgg tggagtctgg gggaggctta gtgcagcctg agggtcccg gaaactctcc     120 tgtgcagcct ctggattcac tttcagtgac tacggaatgg cgtgggttcg acaggctcca     180

```
gggaagggc   ctgagtgggt   tgcattcatt   agttatttgg   catatactgt   cttctatgca      240
gacactgtga   cgggccgatt   caccatctct   agagagaatg   ccaaaaacac   cctgtacctg      300
gaaatgagca   gtctgaggtc   tgaggacaca   gccatgtact   actgttcaag   ggaggcgtac      360 ggggagggt    ttacttactg   gggccaaggg   actctggtca   ctgtctctgc   agccaaaacg      420 acaccccat    ctgtctatcc   actggcccct   ggatctgctg   cccaaactaa   ctccatggtg      480
accctgggat   gcctggtcaa   gggctatttc   cctgagccag   tgacagtgac   ctggaactct      540
ggatccctgt   ccagcggtgt   gcacaccttc   ccagctgtcc   tgcagtctga   cctctacact      600
ctgagcagct   cagtgactgt   cccctccagc   acctggccca   gcgagaccgt   cacctgcaac      660
gttgcccacc   cggccagcag   caccaaggtg   gacaagaaaa   ttgtgcccag   ggattgtggt      720
tgtaagcctt   gcatatgtac   agtcccagaa   gtatcatctg   tcttcatctt   cccccccaaag     780 cccaaggatg   tgctcaccat   tactctgact   cctaaggtca   cgtgtgttgt   ggtagacatc      840
agcaaggata   tcccgaggt    ccagttcagc   tggtttgtag   atgatgtgga   ggtgcacaca      900
gctcagacgc   aaccccggga   ggagcagttc   aacagcactt   tccgctcagt   cagtgaactt      960
cccatcatgc   accaggactg   gctcaatggc   aaggagttca   aatgcagggt   caacagtgca      1020
gctttccctg   cccccatcga   gaaaaccatc   tccaaaacca   aaggcagacc   gaaggctcca      1080
caggtgtaca   ccattccacc   tcccaaggag   cagatggcca   aggataaagt   cagtctgacc      1140
tgcatgataa   cagacttctt   ccctgaagac   attactgtgg   agtggcagtg   gaatgggcag      1200
ccagcggaga   actacaagaa   cactcagccc   atcatggaca   cagatggctc   ttacttcgtc      1260
tacagcaagc   tcaatgtgca   gaagagcaac   tgggaggcag   gaaatacttt   cacctgctct      1320
gtgttacatg   agggcctgca   caaccaccat   actgagaaga   gcctctccca   ctctcctggt      1380
aaatga                                                                          1386
```

<210> SEQ ID NO 12
<211> LENGTH: 461
<212> TYPE: PRT
<213> ORGANISM: Artificial Sequence
<220> FEATURE:
<223> OTHER INFORMATION: SYNTHESIZED

<400> SEQUENCE: 12

```
Met Asp Phe Arg Leu Ser Leu Leu Ile Phe Val Leu Ile Leu Lys Gly
1               5                   10                  15

Val Gln Cys Glu Val Lys Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Asp Tyr Gly Met Ala Trp Val Arg Gln Ala Pro Gly Lys Gly Pro
    50                  55                  60

Glu Trp Val Ala Phe Ile Ser Tyr Leu Ala Tyr Thr Val Phe Tyr Ala
65                  70                  75                  80

Asp Thr Val Thr Gly Arg Phe Thr Ile Ser Arg Glu Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ser Arg Glu Ala Tyr Gly Gly Phe Thr Tyr Trp Gly
        115                 120                 125

Gln Gly Thr Leu Val Thr Val Ser Ala Ala Lys Thr Thr Pro Pro Ser
    130                 135                 140
```

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
            165                 170                 175

Thr Trp Asn Ser Gly Ser Leu Ser Ser Gly Val His Thr Phe Pro Ala
        180                 185                 190

Val Leu Gln Ser Asp Leu Tyr Thr Leu Ser Ser Val Thr Val Pro
    195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
450                 455                 460

<210> SEQ ID NO 13
<211> LENGTH: 702
<212> TYPE: DNA
<213> ORGANISM: Artificial Sequence
<220> FEATURE:
<223> OTHER INFORMATION: SYNTHESIZED

<400> SEQUENCE: 13
atggactttc gggtgcagat ttcagcttc ctgctaatca gtgtcacagt gtccagagga      60
gaaattgtgc tcactcagtc tccagccatc acagctgcat ctctgggca aaaggtcacc     120 atcacctgca gtgccagctc aagtgtaagt tacatgcact ggtaccagca gaagtcaggc     180
acctccccca aaccatggat ttatgaaata tccaaactgg cttctggagt cccagctcgc     240
ttcagtggca gtgggtctgg gacctcttac tctctcacaa tcagcagcat ggaggctgaa     300

```
gatgctgcca tttattactg ccagcagtgg aattatcctc tgtacacgtt cggaggggggg    360 accaagctgg aaataaaacg ggctgatgct gcaccaactg tatccatctt cccaccatcc    420
agtgagcagt taacatctgg aggtgcctca gtcgtgtgct tcttgaacaa cttctacccc    480
aaagacatca atgtcaagtg gaagattgat ggcagtgaac gacaaaatgg cgtcctgaac    540
agttggactg atcaggacag caaagacagc acctacagca tgagcagcac cctcacgttg    600
accaaggacg agtatgaacg acataacagc tatacctgtg aggccactca caagacatca    660
acttcaccca ttgtcaagag cttcaacagg aatgagtgtt ag                       702

<210> SEQ ID NO 14
<211> LENGTH: 233
<212> TYPE: PRT
<213> ORGANISM: Artificial Sequence
<220> FEATURE:
<223> OTHER INFORMATION: SYNTHESIZED

<400> SEQUENCE: 14

Met Asp Phe Arg Val Gln Ile Phe Ser Phe Leu Leu Ile Ser Val Thr
1               5                   10                  15

Val Ser Arg Gly Glu Ile Val Leu Thr Gln Ser Pro Ala Ile Thr Ala
            20                  25                  30

Ala Ser Leu Gly Gln Lys Val Thr Ile Thr Cys Ser Ala Ser Ser Ser
        35                  40                  45

Val Ser Tyr Met His Trp Tyr Gln Gln Lys Ser Gly Thr Ser Pro Lys
    50                  55                  60

Pro Trp Ile Tyr Glu Ile Ser Lys Leu Ala Ser Gly Val Pro Ala Arg
65                  70                  75                  80

Phe Ser Gly Ser Gly Ser Gly Thr Ser Tyr Ser Leu Thr Ile Ser Ser
                85                  90                  95

Met Glu Ala Glu Asp Ala Ala Ile Tyr Tyr Cys Gln Gln Trp Asn Tyr
            100                 105                 110

Pro Leu Tyr Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230
```

ANTIBODIES TO TUMOR ASSOCIATED COMPLEX N-GLYCANS WITH TERMINAL GLCNACβ RESIDUES AND METHODS OF USE THEREOF

CROSS REFERENCE TO RELATED APPLICATIONS

This application claims the benefit of PCT Application PCT/US2016/042435, filed Jul. 15, 2016, which claims the benefit of U.S. Provisional Application No. 62/192,750, filed Jul. 15, 2015, each of the disclosures of which is hereby incorporated by reference in its entirety.

FIELD OF THE INVENTION

The present disclosure relates to antibodies specific for a group of tumor associated complex N-glycans with GlcNAcβ residues and methods for detecting a tumor in a subject. The present disclosure also relates to therapeutic antibodies specific for the group of tumor associated complex N-glycans with GlcNAcβ residues.

BACKGROUND OF THE INVENTION

In 2014, there will be an estimated 1,665,540 new cancer cases diagnosed and 585,720 cancer deaths in the United States. To fight this devastating disease, one of the most important keys is to develop sensitive, accurate, non-invasive, economical, and easily performed assays in the clinic for early cancer detection and diagnosis, monitoring of the disease progression and assessment of treatment response.

Specifically, the top 10 deadliest cancers (lung, colorectal, breast, pancreatic, prostate, leukemia, Non-Hodgkin lymphoma, liver and intrahepatic bile duct, ovarian, and esophageal cancers) are the first leading cause of cancer death in the Western world. In the United States, more than a million new cases of the top 10 cancers are diagnosed and about 420,000 patients die each year. The high mortality partially reflects the lack of universal (pan) tumor specific markers for early tumor detection and diagnosis. In addition, millions of people are at high risk for the top 10 cancers. Those with a high risk for cancer require a reliable and non-invasive test to detect their tumor at early stages. Currently, many tumor markers such as CA19-9, CEA, CA50, CA125, PSA, and CA242 have been investigated for early tumor detection, but none of them are adequate. Furthermore, enzymatic proteins including tumor M2-Pyruvate kinase, elastinase-1 and Galactosyltransferase Isoenzyme II have been explored for cancer diagnosis. The results indicated that those markers seem to have limited value in cancer diagnosis. Non-coding RNAs, macrophage inhibitory cytokine 1 (MIC-1), and CEACAM1 (a member of the CEA antigen family) have also been investigated. Unfortunately, most are still in preclinical evaluation or have limited application in early cancer detection. In summary, no biomarkers or biomarker assays are presently available for cancer early detection and diagnosis. Therefore, tumor specific biological markers and their binding ligands are desperately desired for development of biomarker assays for early cancer detection and diagnosis.

Accordingly, there is a need in the art for a tumor specific, sensitive, non-invasive, economical, and easily performed assay for early cancer detection and diagnosis, monitoring of the disease progression and assessment of treatment response.

SUMMARY OF THE INVENTION

In an aspect, the disclosure provides an isolated antibody that specifically binds tumor associated complex N-glycans with terminal GlcNAcβ residues. In certain embodiments, the antibody comprises an amino acid sequence set forth in SEQ ID NO:7 and SEQ ID NO:8. In other embodiments, the antibody specifically binds tumor associated complex N-glycans with GlcNAcβ residues and comprises a light chain CDR1 comprising the amino acid sequence of SEQ ID NO: 1, a light chain CDR2 comprising the amino acid sequence of SEQ ID NO: 2, a light chain CDR3 comprising the amino acid sequence of SEQ ID NO: 3, a heavy chain CDR1 comprising the amino acid sequence of SEQ ID NO: 4, a heavy chain CDR2 comprising the amino acid sequence of SEQ ID NO: 5, and a heavy chain CDR3 comprising the amino acid sequence of SEQ ID NO: 6. In any of the foregoing embodiments, the antibody is selected from the group consisting of a single-chain antibody, an antibody fragment, a chimeric antibody, a humanized antibody, a bi-specific T cell engager (BiTE) antibody or a chimeric antigen receptor (CAR).

In another aspect, the disclosure provides a method for measuring an amount of tumor associated complex N-glycans with terminal GlcNAcβ residues in a biological sample. The method comprises measuring the amount of tumor associated complex N-glycans with terminal GlcNAcβ residues in a biological sample obtained from a subject using at least one isolated antibody that specifically binds tumor associated complex N-glycans with terminal GlcNAcβ residues, wherein the antibody comprises an amino acid sequence selected from the group consisting of SEQ ID NO: 1-6 with zero to two amino acid substitutions.

In still another aspect, the disclosure provides a method for detecting a tumor in a subject. The method comprises: measuring an amount of tumor associated complex N-glycans with terminal GlcNAcβ residues in a biological sample obtained from a subject using at least one isolated antibody that specifically binds tumor associated complex N-glycans with terminal GlcNAcβ residues, wherein the antibody comprises an amino acid sequence selected from the group consisting of SEQ ID NO: 1-6 with zero to two amino acid substitutions; and comparing the amount of tumor associated complex N-glycans with terminal GlcNAcβ residues in the sample to a reference value, wherein a greater amount of tumor associated complex N-glycans with terminal GlcNAcβ residues in the sample compared to the reference value indicates the presence of a tumor in the subject.

In still yet another aspect, the disclosure provides a method for monitoring response to treatment of a tumor in a subject. The method comprises: (a) measuring an amount of tumor associated complex N-glycans with terminal GlcNAcβ residues in a biological sample obtained from a subject using at least one isolated antibody that specifically binds tumor associated complex N-glycans with terminal GlcNAcβ residues, wherein the antibody comprises an amino acid sequence selected from the group consisting of SEQ ID NO: 1-6 with zero to two amino acid substitutions; (b) measuring the amount of tumor associated complex N-glycans with terminal GlcNAcβ residues in a second biological sample obtained from the subject after initiation of treatment using at least one isolated antibody that specifically binds tumor associated complex N-glycans with terminal GlcNAcβ residues, wherein the antibody comprises an amino acid sequence selected from the group consisting of SEQ ID NO: 1-6 with zero to two amino acid substitutions; and (c) comparing the amount of tumor associated complex N-glycans with terminal GlcNAcβ residues in the first sample to the amount of tumor associated complex N-glycans with terminal GlcNAcβ residues in the second sample, wherein a change in the amount of tumor associated complex N-glycans with terminal GlcNAcβ residues in the samples indicates a response to treatment.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) 2780 ovarian cancer; (FIG. 1B) NSY colon cancer; (FIG. 1C) Panc-1 pancreatic cancer and (FIG. 1D) A427 lung cancer. mAb M9A12 stained plasma membranes of cultured cancer cells because intact membranes of living cells prevent IgG (150 KD) from entering into the cells passively.

(FIG. 8A) adenocarcinoma showing positive staining (brown color) of tumor cells and component in cancerous lumens (open arrow); (FIG. 8B) squamous carcinoma; (FIG. 8C) small cell carcinoma; (FIG. 8D) normal lung tissues showing negative staining in both normal tissues and materials in small bronchi (solid arrow head); (FIG. 8E) chronic bronchitis demonstrating negative staining of normal tissues and component in small bronchi (open arrow head); and (FIG. 8F) chronic bronchitis with epithelial cell hyperplasia exhibiting positive staining in the areas of Golgi complex (solid arrow).

FIG. 10A, FIG. 10B, FIG. 10C, FIG. 10D, FIG. 10E and FIG. 10F depict representative images of immunohistochemical staining of ovarian normal, borderline tumor and cancer tissues with mAb M9A12. Cancer and borderline tumor tissues were stained with the antibody (brown color). (FIG. 10A, FIG. 10B) serous carcinomas; (FIG. 10C, FIG. 10D) mucinous carcinomas; (FIG. 10E) borderline tumor; (FIG. 10F) normal ovarian tissues. Cell nuclei were stained blue with hematoxylin.

DETAILED DESCRIPTION OF THE INVENTION

Figure 1A:
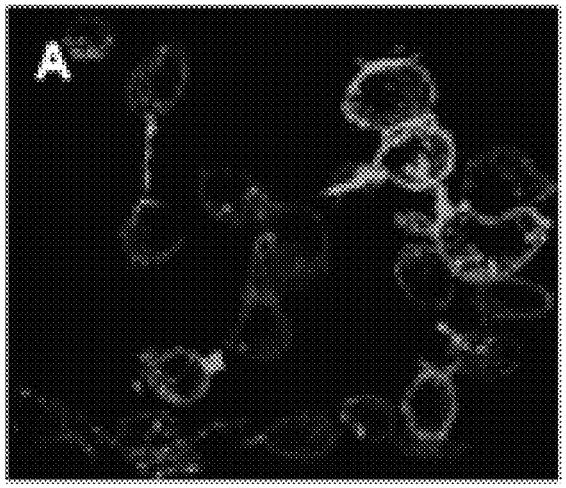
FIG. 1A, FIG. 1B, FIG. 1C and FIG. 1D depict representative images of immunofluorescence staining. Immunofluorescence staining of mAb M9A12 in cultured human cancer cells.
Figure 1B:
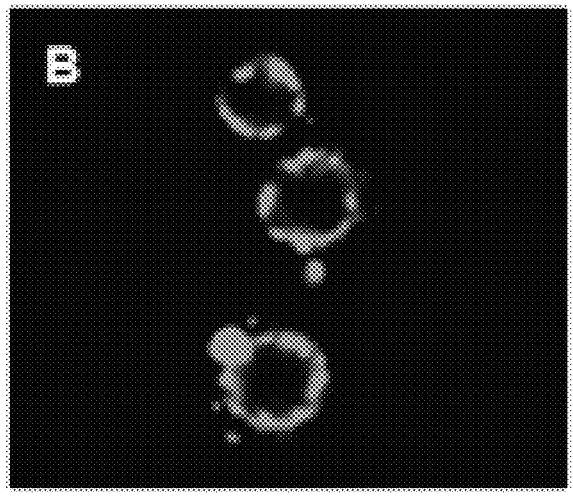

Applicants have developed antibodies and methods of use thereof for detecting cancer in a subject. The method comprises detecting and measuring the amount of tumor associated complex N-glycans with terminal GlcNAcβ residues in a biological sample obtained from a subject using an antibody of the disclosure. The present disclosure encompasses the discovery that tumor associated complex N-glycans with terminal GlcNAcβ residues are a tumor specific antigen that is abundantly expressed on cancer cells, and it is detectable in exosomes isolated from biological samples. It was discovered that mAb M9A12 recognizes tumor associated complex N-glycans with terminal GlcNAcβ residues. Thus, the disclosure provides evidence that detection of an increased amount tumor associated complex N-glycans with terminal GlcNAcβ residues in a biological sample is likely directly related to tumor burden. In an aspect, an increased amount of tumor associated complex N-glycans with terminal GlcNAcβ residues in a biological sample indicates the presence of a tumor. In another aspect, an increased amount of tumor associated complex N-glycans with terminal GlcNAcβ residues in a biological sample indicates tumor burden. In still another aspect, an increased amount of tumor associated complex N-glycans with terminal GlcNAcβ residues in a biological sample indicates tumor progression. In still yet another aspect, an increased amount of tumor associated complex N-glycans with terminal GlcNAcβ residues in a biological sample relative to a previously assessed amount of tumor associated complex N-glycans with terminal GlcNAcβ residues in a biological fluid indicates tumor progression or inefficacy of therapy. In yet still another aspect, antibodies useful in detecting an increased amount of tumor associated complex N-glycans with terminal GlcNAcβ residues in a biological sample include those which bind a terminal GlcNAcβ within tumor associated complex N-glycans. More specifically, antibodies useful in detecting an increased amount of tumor associated complex N-glycans with terminal GlcNAcβ residues in a biological sample include those which bind an epitope within NGA3B. In other aspects, antibodies which bind tumor associated complex N-glycans with terminal GlcNAcβ residues may be used in the treatment of cancer.

I. Anti-Tumor Associated Complex N-Glycan Antibodies

Antibodies to tumor associated complex N-glycans with terminal GlcNAcβ residues useful herein include all antibodies that specifically bind tumor associated complex N-glycans with terminal GlcNAcβ residues. Additionally, antibodies useful herein include all antibodies that specifically bind a terminal GlcNAcβ within tumor associated complex N-glycans. Additionally, antibodies useful herein include all antibodies that specifically bind an epitope within NGA3B glycan. Specifically, anti-NGA3B antibodies useful herein include all antibodies that specifically bind terminal GlcNAcβ within NGA3B glycan. Generally speaking, the epitope recognized by an antibody of the disclosure is detectable on cancerous cells. The epitope recognized by an antibody of the disclosure may or may not be detectable in the absence of cancerous cells. For example, cancerous cells may increase expression of the glycan such that a previously undetectable epitope becomes detectable. Alternatively, an epitope recognized by an antibody of the disclosure may be detectable both in the absence of cancerous cells and the presence of cancerous cells, though the detectable signal is greater in the presence of cancerous cells. Antibodies useful herein also include antibodies that bind to specific regions of tumor associated complex N-glycans. Specific regions of complex N-glycans include, but are not limited to, GlcNAc residues, mannose residues, β1-2 linkages, α1-6 linkages, β1-4 linkages, α1-3 linkages, and β1-6 linkages. In a specific embodiment, antibodies useful herein include antibodies that bind to tumor associated complex N-glycans with terminal GlcNAcβ residues. Other forms of tumor associated complex N-glycans include but are not limited to truncated, modified, soluble, insoluble, intracellular, extracellular forms, as well as tumor associated GlcNAcβ residues on complex N-glycans with other proteins or molecules. Binding of antibodies of the disclosure to terminal GlcNAcβ residues of complex N-glycans may be dependent on protein core, spacing, orientation of the N-glycans, and/or 3-D structure of terminal GlcNAcβ on the presented molecules (proteins and/or lipids).

Antibodies useful herein include those which are isolated, characterized, purified, functional and have been recovered (obtained) from a process for their preparation and thus available for use herein in a useful form in an amount sufficient for an assay to detect and measure the amount of tumor associated complex N-glycans with terminal GlcNAcβ residues in a biological sample.

The term "antibody" includes the term "monoclonal antibody". "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv, regions, of antibodies with this specificity.

Bispecific monoclonal antibodies (i.e. a protein that comprises fragments of two different monoclonal antibodies and consequently binds two different antigens) are also included within the definition of "antibody". A specific example of a bispecific monoclonal antibody may be a Bi-specific T-cell engager (BiTE) which is a fusion protein consisting of two single-chain variable fragments (scFvs) of different antibodies. In certain embodiments, BiTEs forms a link between T cells and tumor cells. Accordingly, one scFv is an antibody of the disclosure and one scFv binds a T cell. More specifically, the scFv that binds a T cell can bind the CD3 receptor. For example, the scFv that binds a T cell can be an anti-CD3 antibody. The bispecific antibody comprising one scFv that is an antibody of the disclosure and one scFv that is an anti-CD3 antibody forms a link between T cells and tumor cells. This interaction causes T cells to exert cytotoxic activity on tumor cells by producing proteins like perforin and granzymes, independently of the presence of MHCI or co-stimulatory molecules. These proteins enter tumor cells and initiate apoptosis. Amino acid residues can be used as a linker between the first and second scFv. Typical amino acid residues used for linking are glycine, serine, alanine, leucine, tyrosine, cysteine, lysine, glutamic and aspartic acid, or the like. For example, a linker can be $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. Accordingly, n can be 1, 2, 3, 4, 5, 6, 7, 8, 9, 10, 11, 12, 13, 14, 15, 16, 17, 18, 19, or 20. In a specific embodiment, a linker can be $(G_4S)_4$.

Additionally, an antibody of the disclosure may be a chimeric antigen receptor (CAR), also referred to as an artificial T cell receptor, a chimeric T cell receptor, or a chimeric immunoreceptor. CARs are engineered receptors, which graft an arbitrary specificity onto an immune effector cell. Typically, these receptors are used to graft the specificity of a monoclonal antibody onto a T cell. CARs are used as a therapy for cancer via adoptive cell transfer. T cells are removed from a subject and modified so that they express a receptor specific to a cancer (i.e. an antibody of the disclosure). The T cells which can then recognize and kill the cancer cells are reintroduced into the subject. Specifically, a CAR can be a fusion of an scFv antibody of the disclosure with the intracellular domain from CD3-zeta (CD3ζ). The CAR can further comprise one or more intracellular signaling domains from various costimulatory protein receptors. Non-limiting examples of costimulatory protein receptors include CD28, 41BB, OX40 and ICOS. In a specific embodiment, a CAR comprises an scFv antibody of the disclosure fused to CD28, 41BB and CD3ζ. The construct can further comprise a linker as described above.

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

The basic antibody structural unit of an antibody useful herein comprises a tetramer. Each tetramer is composed of two identical pairs of polypeptide chains, each pair having one "light' (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites. The chains exhibit the same general structure of relatively conserved framework regions (FR) joined by three hypervariable regions, also called complementarity determining regions (hereinafter referred to as "CDRs"). The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with tumor associated complex N-glycans with terminal GlcNAcβ residues. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an antibody of the disclosure that is composed partially or fully of amino acid sequences derived from a human antibody germ line by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for tumor associated complex N-glycans with terminal GlcNAcβ residues is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an antibody of the disclosure comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, et al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

In all instances, an antibody of the disclosure specifically binds the tumor associated complex N-glycans with terminal GlcNAcβ residues. Specifically, an antibody of the disclosure binds an epitope within complex N-glycans. More specifically, an antibody of the disclosure binds terminal GlcNAcβ residues within complex N-glycans. Additionally, an antibody of the disclosure binds an epitope within NGA3B glycan. The phrase "specifically binds" herein means antibodies bind to the protein with an affinity constant or Affinity of interaction ($K_D$) in the range of at least 0.1 mM to 1 pM, or in the range of at least 0.1 pM to 10 nM, with a preferred range being 0.1 pM to 1 nM. Tumor associated complex N-glycans with terminal GlcNAcβ residues may be found in a variety of species, and methods of determining whether an antibody binds to tumor associated complex N-glycans with terminal GlcNAcβ residues are known in the art. For instance, see the Examples. Accordingly, antibodies of the disclosure may also bind tumor associated complex N-glycans with terminal GlcNAcβ residues from other species.

The antibodies of the present disclosure may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present disclosure are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

The antibodies of the present disclosure, including scFVs, may also be conjugated to a payload, such as a therapeutic agent, a detectable, and/or a delivery device (including, but not limited to, a liposome or a nanoparticle) containing the drug or detectable label. Methods of conjugating an antibody to a therapeutic agent, a detectable label, a liposome, a nanoparticle or other delivery device are known in the art. Generally speaking, the conjugation should not interfere with the antibody recognizing its target, and should not interfere with the active site of the target. In some instances, an antibody may be generated with a cleavable linkage between the antibody and the payload. Such a linker may allow release of the payload at a specific cellular location. Suitable linkers include, but are not limited to, amino acid chains and alkyl chains functionalized with reactive groups for conjugating to both the antibody of the disclosure and the detectable label and/or therapeutic agent. The therapeutic agent, detectable label, and delivery device are described in further detail below.

A preferred antibody is a mouse antibody derived from a hybridoma designated M9A12. As used herein, the term "derived from" means that the "derived" antibody comprises at least one CDR region from the antibody produced by M9A12. Stated another way, the "derived antibody" comprises at least one CDR region comprised of the amino acid sequence selected from the group consisting of SEQ ID NO: 1, 2, 3, 4, 5 and 6.

In one embodiment, an antibody of the disclosure may be derived from the hybridoma M9A12, and may be encoded by a nucleic acid sequence comprising 90, 91, 92, 93, 94, 95, 96, 97, 98, or 99% identity to the light chain variable region of SEQ ID NO:9, or may be encoded by a nucleic acid sequence comprising 90, 91, 92, 93, 94, 95, 96, 97, 98, or 99% identity to the heavy chain variable region of SEQ ID NO:10. In another embodiment, an antibody of the disclosure may be derived from the hybridoma M9A12, and may be encoded by an amino acid sequence comprising 90, 91, 92, 93, 94, 95, 96, 97, 98, or 99% identity to the light chain variable region of SEQ ID NO:7, or may be encoded by a nucleic acid sequence comprising 90, 91, 92, 93, 94, 95, 96, 97, 98, or 99% identity to the heavy chain variable region of SEQ ID NO:8. In each of the above embodiments, the antibody may be humanized.

In an exemplary embodiment of an antibody of the disclosure comprises the light chain amino acid sequence of SEQ ID NO:7 and the heavy chain amino acid sequence of SEQ ID NO:8 [i.e. the monoclonal antibody referred to herein as mAb M9A12]. In another exemplary embodiment of an antibody of the disclosure comprises the light chain nucleic acid sequence of SEQ ID NO:9 and the heavy chain amino acid sequence of SEQ ID NO:10 [i.e. the monoclonal antibody referred to herein as mAb M9A12]. In each of the above embodiments, the antibody may be humanized.

In one embodiment, an antibody of the disclosure may comprise a light chain CDR1, such as the antibody 1 of Table A. In another embodiment, an antibody of the disclosure may comprise a light chain CDR2, such as the antibody 4 of Table A. In yet another embodiment, an antibody of the disclosure may comprise a light chain CDR3, such as the antibody 6 of Table A. In an alternative embodiment, an antibody of the disclosure may comprise a combination of two or three light chain CDRs, such as the antibodies 2, 3 and 5 of Table A. In each of the above embodiments, the antibody may be humanized.

Similarly, in one embodiment, an antibody of the disclosure may comprise a heavy chain CDR1, such as the antibody 7 of Table A. In another embodiment, an antibody of the disclosure may comprise a heavy chain CDR2, such as the antibody 10 of Table A. In yet another embodiment, an antibody of the disclosure may comprise a heavy chain CDR3, such as the antibody 12 of Table A. In an alternative embodiment, an antibody of the disclosure may comprise a combination of two or three heavy chain CDRs, such as the antibodies 8, 9 and 11 of Table A. In each of the above embodiments, the antibody may be humanized.

Alternatively, an antibody of the disclosure may comprise one or more light chain CDRs and one or more heavy chain CDRs, such as the antibodies 13-48 of Table A. In each of the above embodiments, the antibody may be humanized.

TABLE A

| | Light Chain | | | Heavy Chain | | |
|---|---|---|---|---|---|---|
| Antibody | CDR1 | CDR2 | CDR3 | CDR1 | CDR2 | CDR3 |
| 1 | SEQ ID NO: 1 | | | | | |
| 2 | SEQ ID NO: 1 | SEQ ID NO: 2 | | | | |
| 3 | SEQ ID NO: 1 | SEQ ID NO: 2 | SEQ ID NO: 3 | | | |
| 4 | | SEQ ID NO: 2 | | | | |
| 5 | | SEQ ID NO: 2 | SEQ ID NO: 3 | | | |
| 6 | | | SEQ ID NO: 3 | | | |
| 7 | | | | SEQ ID NO: 4 | | |
| 8 | | | | SEQ ID NO: 4 | SEQ ID NO: 5 | |
| 9 | | | | SEQ ID NO: 4 | SEQ ID NO: 5 | SEQ ID NO: 6 |
| 10 | | | | | SEQ ID NO: 5 | |
| 11 | | | | | SEQ ID NO: 5 | SEQ ID NO: 6 |
| 12 | | | | | | SEQ ID NO: 6 |
| 13 | SEQ ID NO: 1 | | | SEQ ID NO: 4 | | |
| 14 | SEQ ID NO: 1 | | | SEQ ID NO: 4 | SEQ ID NO: 5 | |
| 15 | SEQ ID NO: 1 | | | SEQ ID NO: 4 | SEQ ID NO: 5 | SEQ ID NO: 6 |
| 16 | SEQ ID NO: 1 | | | | SEQ ID NO: 5 | |
| 17 | SEQ ID NO: 1 | | | | SEQ ID NO: 5 | SEQ ID NO: 6 |
| 18 | SEQ ID NO: 1 | | | | | SEQ ID NO: 6 |
| 19 | SEQ ID NO: 1 | SEQ ID NO: 2 | | SEQ ID NO: 4 | | |
| 20 | SEQ ID NO: 1 | SEQ ID NO: 2 | | SEQ ID NO: 4 | SEQ ID NO: 5 | |
| 21 | SEQ ID NO: 1 | SEQ ID NO: 2 | | SEQ ID NO: 4 | SEQ ID NO: 5 | SEQ ID NO: 6 |
| 22 | SEQ ID NO: 1 | SEQ ID NO: 2 | | | SEQ ID NO: 5 | |
| 23 | SEQ ID NO: 1 | SEQ ID NO: 2 | | | SEQ ID NO: 5 | SEQ ID NO: 6 |
| 24 | SEQ ID NO: 1 | SEQ ID NO: 2 | | | | SEQ ID NO: 6 |
| 25 | SEQ ID NO: 1 | SEQ ID NO: 2 | SEQ ID NO: 3 | SEQ ID NO: 4 | | |
| 26 | SEQ ID NO: 1 | SEQ ID NO: 2 | SEQ ID NO: 3 | SEQ ID NO: 4 | SEQ ID NO: 5 | |
| 27 | SEQ ID NO: 1 | SEQ ID NO: 2 | SEQ ID NO: 3 | SEQ ID NO: 4 | SEQ ID NO: 5 | SEQ ID NO: 6 |
| 28 | SEQ ID NO: 1 | SEQ ID NO: 2 | SEQ ID NO: 3 | | SEQ ID NO: 5 | |
| 29 | SEQ ID NO: 1 | SEQ ID NO: 2 | SEQ ID NO: 3 | | SEQ ID NO: 5 | SEQ ID NO: 6 |
| 30 | SEQ ID NO: 1 | SEQ ID NO: 2 | SEQ ID NO: 3 | | | SEQ ID NO: 6 |
| 31 | | SEQ ID NO: 2 | | SEQ ID NO: 4 | | |
| 32 | | SEQ ID NO: 2 | | SEQ ID NO: 4 | SEQ ID NO: 5 | |
| 33 | | SEQ ID NO: 2 | | SEQ ID NO: 4 | SEQ ID NO: 5 | SEQ ID NO: 6 |
| 34 | | SEQ ID NO: 2 | | | SEQ ID NO: 5 | |
| 35 | | SEQ ID NO: 2 | | | SEQ ID NO: 5 | SEQ ID NO: 6 |
| 36 | | SEQ ID NO: 2 | | | | SEQ ID NO: 6 |
| 37 | | SEQ ID NO: 2 | SEQ ID NO: 3 | SEQ ID NO: 4 | | |
| 38 | | SEQ ID NO: 2 | SEQ ID NO: 3 | SEQ ID NO: 4 | SEQ ID NO: 5 | |
| 39 | | SEQ ID NO: 2 | SEQ ID NO: 3 | SEQ ID NO: 4 | SEQ ID NO: 5 | SEQ ID NO: 6 |
| 40 | | SEQ ID NO: 2 | SEQ ID NO: 3 | | SEQ ID NO: 5 | |
| 41 | | SEQ ID NO: 2 | SEQ ID NO: 3 | | SEQ ID NO: 5 | SEQ ID NO: 6 |
| 42 | | SEQ ID NO: 2 | SEQ ID NO: 3 | | | SEQ ID NO: 6 |
| 43 | | | SEQ ID NO: 3 | SEQ ID NO: 4 | | |
| 44 | | | SEQ ID NO: 3 | SEQ ID NO: 4 | SEQ ID NO: 5 | |
| 45 | | | SEQ ID NO: 3 | SEQ ID NO: 4 | SEQ ID NO: 5 | SEQ ID NO: 6 |
| 46 | | | SEQ ID NO: 3 | | SEQ ID NO: 5 | |
| 47 | | | SEQ ID NO: 3 | | SEQ ID NO: 5 | SEQ ID NO: 6 |
| 48 | | | SEQ ID NO: 3 | | | SEQ ID NO: 6 |

In one embodiment, an antibody of the disclosure may comprise a light chain variable region comprising a CDR1 of amino acid sequence SEQ ID NO: 1 with zero to two amino acid substitutions, a CDR2 of amino acid sequence SEQ ID NO: 2 with zero to two amino acid substitutions, and a CDR3 of amino acid sequence SEQ ID NO:3 with zero to two amino acid substitutions, or may comprise a heavy chain variable region comprising a CDR1 of amino acid sequence SEQ ID NO: 4 with zero to two amino acid substitutions, a CDR2 of amino acid sequence SEQ ID NO: 5 with zero to two amino acid substitutions, and a CDR3 of amino acid sequence SEQ ID NO: 6 with zero to two amino acid substitutions. In a preferred embodiment, an antibody of the disclosure may comprise a light chain variable region comprising a CDR1 of amino acid sequence SEQ ID NO: 1 with zero to two amino acid substitutions, a CDR2 of amino acid sequence SEQ ID NO: 2 with zero to two amino acid substitutions, a CDR3 of amino acid sequence SEQ ID NO:3, a heavy chain variable region comprising a CDR1 of amino acid sequence SEQ ID NO: 4 with zero to two amino acid substitutions, a CDR2 of amino acid sequence SEQ ID NO: 5 with zero to two amino acid substitutions, and a CDR3 of amino acid sequence SEQ ID NO: 6 with zero to two amino acid substitutions. In an exemplary embodiment, an antibody of the disclosure may comprise a light chain variable region comprising a CDR1 of amino acid sequence SEQ ID NO: 1, a CDR2 of amino acid sequence SEQ ID NO: 2, a CDR3 of amino acid sequence SEQ ID NO:3, a heavy chain variable region comprising a CDR1 of amino acid sequence SEQ ID NO: 4, a CDR2 of amino acid sequence SEQ ID NO: 5, and a CDR3 of amino acid sequence SEQ ID NO: 6. The disclosure also encompasses the corresponding nucleic acid sequences of SEQ ID NO:1, 2, 3, 4, 5, and 6, which can readily be determined by one of skill in the art, and may be incorporated into a vector or other large DNA molecule, such as a chromosome, in order to express an antibody of the disclosure. In each of the above embodiments, the antibody may be humanized.

(a) Detectable Label

In an aspect, an antibody of the disclosure may be conjugated to a detectable label. A detectable label may be directly conjugated to an antibody of the disclosure or may be indirectly conjugated to an antibody of the disclosure. In an embodiment, a detectable label may be complexed with a chelating agent that is conjugated to an antibody of the disclosure. In another embodiment, a detectable label may be complexed with a chelating agent that is conjugated to a linker that is conjugated to an antibody of the disclosure. In still another embodiment, a detectable label may be conjugated to a linker that is conjugated to an antibody of the disclosure. In still yet another embodiment, a detectable label may be indirectly attached to an antibody of the disclosure by the ability of the label to be specifically bound by a second molecule. One example of this type of an indirectly attached label is a biotin label that can be specifically bound by the second molecule, streptavidin or other biotin binding protein. Single, dual or multiple labeling may be advantageous. An isolated antibody of the present disclosure may be conjugated to one, two, three, four, or five types of detectable labels.

As used herein, a "detectable label" is any type of label which, when attached to an antibody of the disclosure renders the antibody detectable. A detectable label may also be toxic to cells or cytotoxic. Accordingly, a detectable label may also be a therapeutic agent or cytotoxic agent. In general, detectable labels may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present disclosure.

A detectable label emits a signal that can be detected by a signal transducing machine. In some cases, the detectable label can emit a signal spontaneously, such as when the detectable label is a radionuclide. In other cases the detectable label emits a signal as a result of being stimulated by an external field such as when the detectable label is a relaxivity metal. Examples of signals include, without limitation, gamma rays, X-rays, visible light, infrared/near infrared energy, and radiowaves. Examples of signal transducing machines include, without limitation, gamma cameras including SPECT/CT devices, PET scanners, fluorimeters, and Magnetic Resonance Imaging (MRI) machines. As such, the detectable label comprises a label that can be detected using magnetic resonance imaging, scintigraphic imaging, ultrasound, or fluorescence. In a specific embodiment, the detectable label comprises a label that can be detected using positron emission tomography, single photon emission computed tomography, gamma camera imaging, or rectilinear scanning.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. $B_{12}$ or an analog thereof can be labeled for fluorescence detection by labeling the agent with a fluorophore using techniques well known in the art (see, e.g., Lohse et al., Bioconj Chem 8:503-509 (1997)). For example, many known dyes are capable of being coupled to $NH_2$-terminal groups. Alternatively, a fluorochrome such as fluorescein may be bound to a lysine residue of a peptide linker. In a specific embodiment, an alkyne modified dye, such an Alexa Fluor dye, may be clicked to an azido modified $B_{12}$ using, for example, Sharpless click chemistry (Kolb et al., Angew Chem Int Ed 2001; 40: 2004-2021, which incorporated by reference in its entirety).

A radionuclide may be a γ-emitting radionuclide, Auger-emitting radionuclide, β-emitting radionuclide, an α-emitting radionuclide, or a positron-emitting radionuclide. A radionuclide may be a detectable label and/or a therapeutic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97,103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived there from. In a specific embodiment, a radionuclide is selected from the group consisting of copper-64, zirconium-89, yttrium-86, yttrium-90, technetium-99m, iodine-125, iodine-131, lutetium-177, rhenium-186 and rhenium-188.

A variety of metal atoms may be used as a detectable label. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms may be metal ions in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

In an embodiment where an antibody of the disclosure is conjugated to a non-radioactive isotope, it may be used in neutron capture therapy (NCT). Neutron capture therapy (NCT) is a noninvasive therapeutic modality for treating locally invasive malignant tumors. NCT is a two-step procedure: first, the subject is injected with a tumor localizing drug containing a non-radioactive isotope that has a high propensity or cross section (a) to capture slow neutrons. The cross section of the capture agent is many times greater than that of the other elements present in tissues such as hydrogen, oxygen, and nitrogen. In the second step, the subject is radiated with epithermal neutrons, which after losing energy as they penetrate tissue, are absorbed by the capture agent, which subsequently emits high-energy charged particles, thereby resulting in a biologically destructive nuclear reaction. In certain embodiments, the non-radioactive isotope may be boron-10 or gadolinium.

(b) Therapeutic Agent

In an aspect, an antibody of the disclosure may be conjugated to a therapeutic agent, such that the therapeutic agent can be selectively targeted to a cell expressing a tumor associated complex N-glycans with terminal GlcNAcβ residues. The therapeutic agent may be directly conjugated to an antibody of the disclosure or may be indirectly conjugated to an antibody of the disclosure. In an embodiment, the therapeutic agent may be complexed with a chelating agent that is conjugated to an antibody of the disclosure. In another embodiment, the therapeutic agent may be complexed with a chelating agent that is conjugated to a linker that is conjugated to an antibody of the disclosure. In still another embodiment, the therapeutic agent may be conjugated to a linker that is conjugated to an antibody of the disclosure. In still yet another embodiment, the therapeutic agent may be conjugated to a linker that is conjugated to a chelating agent that is complexed with a detectable label and conjugated to an antibody of the disclosure.

A "therapeutic agent" is any compound known in the art that is used in the detection, diagnosis, or treatment of a condition or disease. Such compounds may be naturally-occurring, modified, or synthetic. Non-limiting examples of therapeutic agents may include drugs, therapeutic compounds, toxins, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Such therapeutic agents may be water soluble or may be hydrophobic. Non-limiting examples of therapeutic agents may include immune-related agents, thyroid agents, respiratory products, antineoplastic agents, anti-helmintics, anti-malarials, mitotic inhibitors, hormones, toxins, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of therapeutic agents are described below. In a specific embodiment, a therapeutic agent may be a compound used in the detection diagnosis or treatment of cancer. The therapeutic agent preferably reduces or interferes with tumor growth or otherwise reduces the effect of the tumor within the body or organism. A therapeutic agent that reduces the symptoms produced by the tumor or reduces tumor growth is suitable for the present disclosure. Additionally, any therapeutic agent that reduces the symptoms associated with tumor cell growth will work for purposes of the present disclosure.

An antibody of the disclosure may be conjugated to one, two, three, four, or five therapeutic agents. A linker may or may not be used to conjugate a therapeutic agent to an antibody of the disclosure. Generally speaking, the conjugation should not interfere with the antibody binding. In some instances, an antibody of the disclosure may be generated with a cleavable linkage between the antibody and therapeutic agent. Such a linker may allow release of the therapeutic agent at a specific cellular location. In other instances, an antibody of the disclosure may be generated with an enzyme linked to it to create a prodrug. For example, cytidine deaminase may be linked to an antibody of the disclosure. The cytidine deaminase then cleaves the prodrug to create a cytotoxic drug.

A therapeutic agent of the disclosure may be a toxin. The term "toxin" means the toxic material or product of plants, animals, microorganisms (including, but not limited to, bacteria, viruses, fungi, rickettsiae or protozoa), or infectious substances, or a recombinant or synthesized molecule, whatever their origin and method of production. A toxin may be a small molecule, peptide, or protein that is capable of causing disease on contact with or absorption by body tissues interacting with biological macromolecules such as enzymes or cellular receptors. A toxin may be a "biotoxin" which is used to explicitly identify the toxin as from biological origin. Biotoxins may be further classified into fungal biotoxins, or short mycotoxins, microbial biotoxins, plant biotoxins, short phytotoxins and animal biotoxins. Non-limiting examples of biotoxins include: endotoxins produced by bacteria, such as *Pseudomonas* endotoxin; cyanotoxins produced by cyanobacteria, such as microcystins, nodularins, anatoxin-a, cylindrospermopsins, lyngbyatoxin-a, saxitoxin, lipopolysaccharides, aplysiatoxins, BMAA; dinotoxins produced by dinoflagellates, such as saxitoxins and gonyautoxins; necrotoxins produced by, for example, the brown recluse or "fiddle back" spider, most rattlesnakes and vipers, the puff adder, *Streptococcus pyogenes*; neurotoxins produced by, for example, the black widow spider, most scorpions, the box jellyfish, elapid snakes, the cone snail, the Blue-ringed octopus, venomous fish, frogs, palythoa coral, various different types of algae, cyanobacteria and dinoflagellates, such as botulinum toxin (e.g. Botox), tetanus toxin, tetrodotoxin, chlorotoxin, conotoxin, anatoxin-a, bungarotoxin, caramboxin, curare; myotoxins, found in, for example, snake and lizard venoms; and cytotoxins such as ricin, from castor beans, apitoxin, from honey bees, and T-2 mycotoxin, from certain toxic mushrooms. In certain embodiments, a toxin is a cytotoxin. In an embodiment, a cytotoxin is an endotoxin from *Pseudomonas*.

A therapeutic agent of the disclosure may be a small molecule therapeutic, a therapeutic antibody, a therapeutic nucleic acid, or a chemotherapeutic agent. Non-limiting examples of therapeutic antibodies may include muromomab, abciximab, rituximab, daclizumab, basiliximab, palivizumab, infliximab, trastuzumab, etanercept, gemtuzumab, alemtuzumab, ibritomomab, adalimumab, alefacept, omalizumab, tositumomab, efalizumab, cetuximab, bevacizumab, natalizumab, ranibizumab, panitumumab, eculizumab, and certolizumab. A representative therapeutic nucleic acid may encode a polypeptide having an ability to induce an immune response and/or an anti-angiogenic response in vivo. Representative therapeutic proteins with immunostimulatory effects include but are not limited to cytokines (e.g., an interleukin (IL) such as IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein. Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991). Representative proteins with both immunostimulatory and anti-angiogenic activities may include IL12, interferon-γ, or a chemokine. Other therapeutic nucleic acids that may be useful for cancer therapy include but are not limited to nucleic acid sequences encoding tumor suppressor gene products/antigens, antimetabolites, suicide gene products, and combinations thereof.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. A cytotoxic agent is any naturally-occurring, modified, or synthetic compound that is toxic to tumor cells. Such agents are useful in the treatment of neoplasms, and in the treatment of other symptoms or diseases characterized by cell proliferation or a hyperactive cell population. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites may include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non limiting examples of angiogeneisis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1BB ligand, and Apo-1 ligand.

Non-limiting examples of photodynamic therapeutic agents may include aminolevulinic acid, methyl aminolevulinate, retinoids (alitretinon, tamibarotene, tretinoin), and temoporfin.

Other antineoplastic agents may include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The dose of the chemotherapeutic agent can and will vary depending upon the agent and the type of tumor or neoplasm. A skilled practitioner will be able to determine the appropriate dose of the chemotherapeutic agent.

Other therapeutic agents may comprise a virus or a viral genome such as an oncolytic virus. An oncolytic virus comprises a naturally occurring virus that is capable of killing a cell in the target tissue (for example, by lysis) when it enters such a cell.

(c) Delivery Vehicle

An antibody of the disclosure may be conjugated to a vehicle for cellular delivery. In these embodiments, typically an antibody of the disclosure, which may or may not be conjugated to a detectable label and/or therapeutic agent, is encapsulated in a suitable vehicle to either aid in the delivery of the compound to target cells, to increase the stability of the antibody, or to minimize potential toxicity of the antibody. As will be appreciated by a skilled artisan, a variety of vehicles are suitable for delivering an antibody of the present disclosure. Non-limiting examples of suitable structured fluid delivery systems may include nanoparticles, liposomes, microemulsions, micelles, dendrimers and other phospholipid-containing systems. Methods of incorporating antibodies into delivery vehicles are known in the art. Although various embodiments are presented below, it will be appreciate that other methods known in the art to incorporate an antibody of the disclosure into a delivery vehicle are contemplated.

In one alternative embodiment, a liposome delivery vehicle may be utilized. Liposomes, including exosomes released from mAb M9A12 hybridoma cells, depending upon the embodiment, are suitable for delivery of the antibody of the disclosure in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the antibody of the disclosure may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the antibody of the disclosure (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, an antibody of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the disclosure generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The antibody of the disclosure may be encapsulated in a microemulsion by any method generally known in the art.

In yet another embodiment, an antibody of the disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate antibodies of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the disclosure. Generally, the size of dendrimers may range from about 1 nm to about 100 nm.

II. Methods of Using Antibodies of the Disclosure

In an aspect, the present disclosure provides antibodies to detect the tumor associated complex N-glycans with terminal GlcNAcβ residues in a biological sample obtained from a subject. In another aspect, the present disclosure provides antibodies to measure the amount of tumor associated complex N-glycans with terminal GlcNAcβ residues in a biological sample obtained from a subject. The amount of tumor associated complex N-glycans with terminal GlcNAcβ residues in a biological sample obtained from a subject can be used to classify a subject as having high or low amounts of tumor associated complex N-glycans with terminal GlcNAcβ residues, and may be further used to identify the presence of a tumor within the subject. In certain embodiments, exosomes may be isolated from the biological sample prior to detecting or measuring the amount of tumor associated complex N-glycans with terminal GlcNAcβ residues in the biological sample.

(a) Methods to Detect and Measure the Amount of Tumor Associated Complex N-Glycans with Terminal GlcNAcβ Residues in a Biological Sample In an aspect, the disclosure provides means to detect tumor associated complex N-glycans with terminal GlcNAcβ residues in a biological sample obtained from a subject. In another aspect, the disclosure provides means to measure the amount of tumor associated complex N-glycans with terminal GlcNAcβ residues in a biological sample obtained from a subject. The method generally comprises detecting and/or measuring the amount of tumor associated complex N-glycans with terminal GlcNAcβ residues in a biological sample obtained from a subject using an antibody of the disclosure. In certain embodiments, the method comprises (i) isolating exosomes from a biological sample obtained from a subject, and (ii) detecting and/or measuring the amount of tumor associated complex N-glycans with terminal GlcNAcβ residues in the exosome sample using an antibody of the disclosure. Suitable antibodies are described above in Section I.

As used herein, the term "biological sample" refers to a sample obtained from a subject. Any biological sample containing tumor associated complex N-glycans with terminal GlcNAcβ residues is suitable. Numerous types of biological samples are known in the art. Suitable biological sample may include, but are not limited to, tissue samples or bodily fluids. In some embodiments, the biological sample is a tissue sample such as a tissue biopsy. The tissue biopsy may be a biopsy of a known or suspected tumor. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. The sample may also be primary and/or transformed cell cultures derived from tissue from the subject. In other embodiments, the sample may be a bodily fluid. Non-limiting examples of suitable bodily fluids include blood, plasma, serum, urine, saliva, sputum, ascites, tears, mucus from gastrointestinal tracts, and pleural effusion. The fluid may be used "as is", the cellular components may be isolated from the fluid, or a protein fraction may be isolated from the fluid using standard techniques. In a specific embodiment, exosomes may be enriched and isolated from the biological sample. This may be done via methods standard in the art, for example, see Thery et al., *Curr Protoc Cell Biol* 2006; Chapter 3; Unit 3.22, or the Examples.

Suitable subjects include, but are not limited to, a human, a livestock animal, a companion animal, a lab animal, and a zoological animal. A subject may or may not be known to have cancer. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. In a preferred embodiment, the subject is human.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that tumor associated complex N-glycans with terminal GlcNAcβ residues can be accurately detected and the amount measured according to the disclosure.

Once a sample is obtained, it is processed in vitro to detect and measure the amount of tumor associated complex N-glycans with terminal GlcNAcβ residues using an antibody of the disclosure. All suitable methods for detecting and measuring an amount of protein using an antibody known to one of skill in the art are contemplated within the scope of the disclosure. Methods for detecting and measuring an amount of protein using an antibody (i.e. "antibody-based methods") are well known in the art. Non-limiting examples include an ELISA, an ExoELISA, a sandwich immunoassay, a radioimmunoassay, an immunoblot or Western blot, flow cytometry, immunohistochemistry, an array and a Microfluidic chip based assays.

In general, an antibody-based method of detecting and measuring an amount of tumor associated complex N-glycans with terminal GlcNAcβ residues comprises contacting some of the sample, or all of the sample, comprising tumor associated complex N-glycans with terminal GlcNAcβ residues with an antibody of the disclosure under conditions effective to allow for formation of a complex between the antibody and the tumor associated complex N-glycans with terminal GlcNAcβ residues. Typically, the entire sample is not needed, allowing one skilled in the art to repeatedly detect and measure the amount of tumor associated complex N-glycans with terminal GlcNAcβ residues in the sample. The method may occur in solution, or the antibody or tumor associated complex N-glycans with terminal GlcNAcβ residues comprising the sample may be immobilized on a solid surface. Non-limiting examples of suitable surfaces may include microtitre plates, test tubes, slides, beads, magnetic beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An antibody of the disclosure may also be attached to the substrate non-covalently. For example, a biotinylated antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the antibody composition of the disclosure to the sample and incubating the mixture for a period of time long enough for the antibody to bind to any antigen present. After this time, the complex will be washed and the complex may be detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an antibody of the disclosure. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one antibody of the disclosure. The antibody attached to the substrate is located at one or more spatially defined addresses of the array. For example, an array may comprise at least one, at least two, at least three, at least four, or at least five antibodies, each antibody recognizing the same or different tumor associated complex N-glycans with terminal GlcNAcβ residues, and each antibody may be at one, two, three, four, five, six, seven, eight, nine, ten or more spatially defined addresses.

For each of the foregoing embodiments, the tumor associated complex N-glycans with terminal GlcNAcβ residues may be first isolated or enriched before detection. For instance, the tumor associated complex N-glycans with terminal GlcNAcβ residues may be enriched or isolated using liquid chromatography, by precipitation, electrophoresis, affinity purification, or by exosome isolation. In some embodiments, the tumor associated complex N-glycans with terminal GlcNAcβ residues may be enriched or purified using liquid chromatography. In other embodiments, the tumor associated complex N-glycans with terminal GlcNAcβ residues may be enriched or purified using electrophoresis. In specific embodiments, the tumor associated complex N-glycans with terminal GlcNAcβ residues may be enriched or isolated using exosome isolation. The exosome isolation may comprise exosome bound tumor associated complex N-glycans with terminal GlcNAcβ residues.

In certain embodiments, the tumor associated complex N-glycans with terminal GlcNAcβ residues may be enriched or purified by affinity purification before detection. Specifically, the tumor associated complex N-glycans with terminal GlcNAcβ residues may be enriched or purified by affinity purification using an antibody of the disclosure. Methods of enriching a sample for a glycan or purifying a glycan using affinity purification are known in the art. In short, affinity purification comprises incubating a sample with a solid support, such as beads, a culture plate, or a membrane, that facilitates later steps. A solid support may be coated with an antibody of the disclosure, causing the tumor associated complex N-glycans with terminal GlcNAcβ residues to attach to the solid support. Alternatively, a sample may be incubated with an antibody of the disclosure, and the antibody complex may be isolated by incubating with a solid support coated with a second antibody with specificity to an antibody of the disclosure, causing a glycan-antibody complex to attach to the solid support. The tumor associated complex N-glycans with terminal GlcNAcβ residues may then be purified or enriched by washing other material in the sample that is not bound to the solid support, or, if the solid support is superparamagnetic beads, the tumor associated complex N-glycans with terminal GlcNAcβ residues attached to the beads may be separated from the sample by attraction to a strong magnetic field. Upon enrichment or purification, the tumor associated complex N-glycans may then be detected in the enriched or purified sample using any of the methods described above.

(b) Methods to Detect a Tumor in a Subject

In aspect, the disclosure provides means to classify a subject based on the amount of tumor associated complex N-glycans with terminal GlcNAcβ residues measured in a biological sample obtained from the subject. The method generally comprises (i) measuring the amount of tumor associated complex N-glycans with terminal GlcNAcβ residues in a biological sample obtained from a subject using an antibody of the disclosure, (ii) comparing the amount of tumor associated complex N-glycans with terminal GlcNAcβ residues in the sample to a reference value, and (iii) classifying the subject as having a high or low amount of tumor associated complex N-glycans with terminal GlcNAcβ residues based on the amount of tumor associated complex N-glycans with terminal GlcNAcβ residues measured in the sample. Methods for obtaining a biological sample from a subject and measuring the amount of tumor associated complex N-glycans with terminal GlcNAcβ residues in the sample using an antibody of the disclosure are detailed above and further described in the Examples. In a preferred embodiment, the biological sample is biological fluid selected from the group consisting of blood, plasma, serum, saliva, sputum, ascites, pleural effusion and urine. In a specific embodiment, exosomes may or may not be isolated from the biological sample prior to measuring the amount of tumor associated complex N-glycans with terminal GlcNAcβ residues in the sample.

Any suitable reference value known in the art may be used. For example, a suitable reference value may be the amount of tumor associated complex N-glycans with terminal GlcNAcβ residues in a biological fluid sample obtained from a subject or group of subjects of the same species that has no detectable cancer. In another example, a suitable reference value may be the amount of tumor associated complex N-glycans with terminal GlcNAcβ residues in biological fluid sample obtained from a subject or group of subjects of the same species that has detectable cancer as measured via standard methods such as imaging. In another example, a suitable reference value may be a measurement of the amount of tumor associated complex N-glycans with terminal GlcNAcβ residues in a reference sample obtained from the same subject. The reference sample comprises the same type of biological fluid as the test sample, and may or may not be obtained from the subject when cancer was not suspected. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began.

According to the disclosure, a subject may be classified based on the amount of tumor associated complex N-glycans with terminal GlcNAcβ residues measured in the sample. Classifying a subject based on the amount of tumor associated complex N-glycans with terminal GlcNAcβ residues measured in a sample of biological fluid obtained from the subject may be used to identify subjects with a tumor. Generally speaking, a subject may be classified as having a high or low amount of tumor associated complex N-glycans with terminal GlcNAcβ residues compared to a reference value, wherein a high amount of tumor associated complex N-glycans with terminal GlcNAcβ residues is an amount above the reference value and a low amount is an amount equal to or below the reference value. In preferred embodiments, to classify a subject as having a high amount of tumor associated complex N-glycans with terminal GlcNAcβ residues, the amount of tumor associated complex N-glycans with terminal GlcNAcβ residues in the sample compared to the reference value may be at least 5% greater. For example, the amount of tumor associated complex N-glycans with terminal GlcNAcβ residues in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of tumor associated complex N-glycans with terminal GlcNAcβ residues in the sample of biological fluid obtained from the subject compared to the reference value may be increased at least 2-fold. For example, the amount of tumor associated complex N-glycans with terminal GlcNAcβ residues in the sample compared to the reference value may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold.

In another aspect, the disclosure provides means to detect a tumor in a subject. As such, the methods of the disclosure may be used to detect a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In an embodiment, the neoplasm or cancer is selected from the group consisting of pancreatic cancer, ovarian cancer, lung cancer, stomach cancer, colon cancer and esophageal and tongue/pharynx/larynx cancers. In specific embodiments, the neoplasm or cancer is pancreatic cancer. In other specific embodiments, the neoplasm or cancer is ovarian cancer. In still other specific embodiments, the neoplasm or cancer is lung cancer. In a different embodiment, the neoplasm or cancer is esophageal or tongue/pharynx/larynx cancer.

Upon detection of a tumor, the subject may be treated via methods standard in the art for treating cancer. Such treatment methods may depend on the type and severity of the cancer, as well as the general condition of the patient. Treatment of cancer consists primarily of radiation, surgery, chemotherapy and/or targeted therapy. Standard treatment algorithms for each cancer may be found via the National Comprehensive Cancer Network (NCCN) guidelines (www.nccn.org/professionals/physician_gls/f_guidelines.asp).

Furthermore, methods of the disclosure may be used in the detection, characterization and/or determination of the localization of a tumor ranging from early to late stage disease. Additionally, methods of the disclosure may find utility in staging a cancer, i.e., determining the severity of the cancer, monitoring the progression (worsening) of the cancer, and/or monitoring the regression (improvement). Methods of the disclosure may also be used in the prognosis of a cancer or in monitoring the response to treatment.

In an embodiment, a method for monitoring cancer in a subject may be used to determine disease progression. In such an embodiment, a method of detecting tumor associated complex N-glycans with terminal GlcNAcβ residues may be used to assess the risk of a subject at one point in time, then at a later time, the method of detecting tumor associated complex N-glycans with terminal GlcNAcβ residues may be used to determine the change in risk of the subject over time. For example, the method of detecting tumor associated complex N-glycans with terminal GlcNAcβ residues may be used on the same subject days, weeks, months or years following the initial determination of the amount of tumor associated complex N-glycans with terminal GlcNAcβ residues. Accordingly, the method of detecting tumor associated complex N-glycans with terminal GlcNAcβ residues may be used to follow a subject to determine when the risk of progressing to more severe disease is high thereby requiring treatment. Additionally, the method of detecting tumor associated complex N-glycans with terminal GlcNAcβ residues may be used to measure the rate of disease progression. For example, a depressed amount of tumor associated complex N-glycans with terminal GlcNAcβ residues may indicate an abatement of disease progression. Alternatively, an elevated amount of tumor associated complex N-glycans with terminal GlcNAcβ residues may indicate disease progression.

In another embodiment, a method for monitoring cancer in a subject may also be used to determine the response to treatment. As used herein, patients who respond to treatment are said to have benefited from treatment. Typical responses to treatment measured in clinical practice include, but are not limited to, overall survival, event free survival, time to progression, time to death, partial response (PR), very good partial response (VGPR) and complete response (CR). These terms are well known in the art and are intended to refer to specific parameters measured during clinical trials and in clinical practice by a skilled artisan. For example, a method to detect tumor associated complex N-glycans with terminal GlcNAcβ residues may be performed on the biological sample of the subject prior to initiation of treatment, then at a later time, a method to detect tumor associated complex N-glycans with terminal GlcNAcβ residues may be used to determine the response to treatment over time. For example, a method to detect tumor associated complex N-glycans with terminal GlcNAcβ residues may be performed on the biological sample of the same subject days, weeks, months or years following initiation of treatment. Accordingly, a method to detect tumor associated complex N-glycans with terminal GlcNAcβ residues may be used to follow a subject receiving treatment to determine if the subject is responding to treatment. If the amount of tumor associated complex N-glycans with terminal GlcNAcβ residues remains the same or decreases, then the subject may be responding to treatment. If the amount of tumor associated complex N-glycans with terminal GlcNAcβ residues increases, then the subject may not be responding to treatment. These steps may be repeated to determine the response to therapy over time.

For each aspect, the method generally comprises (i) measuring the amount of tumor associated complex N-glycans with terminal GlcNAcβ residues in a biological sample obtained from a subject using an antibody of the disclosure, and (ii) comparing the amount of tumor associated complex N-glycans with terminal GlcNAcβ residues in the sample to a reference value. A greater amount of tumor associated complex N-glycans with terminal GlcNAcβ residues in the sample compared to the reference value indicates the presence of a tumor. The amount of tumor associated complex N-glycans with terminal GlcNAcβ residues may be a qualitative, a semi-quantitative or quantitative measurement. Suitable antibodies are described above, as are methods for measuring the amount of tumor associated complex N-glycans with terminal GlcNAcβ residues in a biological sample. In a preferred embodiment, the biological sample is biological fluid selected from the group consisting of blood, plasma, and serum. In specific embodiment, exosomes are isolated from the biological sample prior to measuring the amount of tumor associated complex N-glycans with terminal GlcNAcβ residues.

In certain embodiments, the method of the disclosure may be combined with the detection of other known biomarkers for cancer. For example, CA19-9, carcinoembryonic antigen (CEA), CA-125, CA50, CA242, tumor M2-Pyruvate kinase, elastinase-1, galactosyltransferase isoenzyme II, alpha-fetoprotein, macrophage inhibitory cytokine 1 (MIC-1), CEACAM1 and non-coding RNAs. Many of these biomarkers are not specific or sensitive for the detection of cancer or may only be present in a proportion of cancers or are only detectable later in cancer. However, when used in combination with tumor associated complex N-glycans with terminal GlcNAcβ residues such biomarkers may enhance the utility of the tumor associated complex N-glycans with terminal GlcNAcβ residues in cancer detection and diagnosis.

(c) Tumor Specific Delivery

In another aspect, the present disclosure provides a method of delivering a therapeutic agent to a cell expressing tumor associated complex N-glycans with terminal GlcNAcβ residues. Accordingly, an antibody of the present disclosure conjugated to a payload, a bispecific antibody, or a CAR, as described in Section I, may be used in treating, stabilizing and preventing cancer and associated diseases in a subject. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of an antibody of the disclosure is at least 2, 5, 10, 20, or 50-fold greater than the decrease in the number of non-tumor or non-cancerous cells. Desirably, the methods of the present disclosure result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

In yet another aspect, the present disclosure provides a method of detecting a tumor in a subject. The method comprises administering to the subject an antibody of the disclosure conjugated to a detectable label, and detecting the detectable label to detect the presence of tumor associated complex N-glycans with terminal GlcNAcβ residues, wherein the presence of tumor associated complex N-glycans with terminal GlcNAcβ residues indicates the presence of a tumor in the subject. In preferred embodiments, the method may be used to diagnose or image a cancer in a subject. In some embodiments, a method for detecting a tumor can comprise (a) biopsing a suspected tumor; (b) contacting an antibody of the disclosure with the suspected tumor in vitro; and (c) detecting the detectable label, whereby a tumor is diagnosed.

Binding may be detected using microscopy (fluorescent microscopy, confocal microscopy, or electron microscopy), magnetic resonance imaging (including MTI, MRS, DWI and fMRI), scintigraphic imaging (SPECT (Single Photon Emission Computed Tomography), PET (Positron Emission Tomography), gamma camera imaging, and rectilinear scanning), radiography, or ultrasound. The detectable label may be detectable in situ, in vivo, ex vivo, and in vitro.

The antibody compositions, subject, cancer, and therapeutic agents are as described above. The administration of the compositions is described below.

In certain aspects, a pharmacologically effective amount of an antibody of the disclosure, including immunologically reactive fragments, may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living patient could be made up to contain 1 mL sterile buffered water of phosphate buffered saline and about 1-1000 mg of any one of or a combination of the humanized antibody of the present discovery. In a specific embodiment, the antibody composition may have 50-300 mg of antibody per administration. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in antibody concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antibody stability (chemical and physical) and comfort to the patient when administered. Generally, a pH between 4 and 8 is tolerated. Doses will vary from individual to individual based on size, weight, and other physiobiological characteristics of the individual receiving the successful administration.

For therapeutic applications, a therapeutically effective amount of a composition of the disclosure is administered to a subject. A "therapeutically effective amount" is an amount of the therapeutic composition sufficient to produce a measurable biological tumor response (e.g., a cytotoxic response, or tumor regression). Actual dosage levels of active ingredients in a therapeutic composition of the disclosure can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about 0.01 mg/kg to about 100 mg/kg of an antibody described herein. Doses can range from about 0.05 mg/kg to about 50 mg/kg, more preferably from about 0.1 mg/kg to about 25 mg/kg.

For diagnostic applications, a detectable amount of a composition of the disclosure is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled antibody prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as antibodies, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

TABLE B

Sequence listings

| SEQ ID NO: | Description | SEQUENCE |
|---|---|---|
| 1 | mAb M9A12 LC CDR1 | SASSSVSYMH |
| 2 | mAb M9A12 LC CDR2 | EISKLAS |
| 3 | mAb M9A12 LC CDR3 | QQWNYPLYT |
| 4 | mAb M9A12 HC CDR1 | GFTFSDYGMA |
| 5 | mAb M9A12 HC CDR2 | FISYLAYTVFYADTVTG |
| 6 | mAb M9A12 HC CDR3 | EAYGGGFTY |
| 7 | mAb M9A12 Light Chain Variable Domain Amino Acid Sequence | FR1-CDR1-FR2-CDR2-FR3-CDR3-FR4<br>EIVLTQSPAITAASLGQKVTITCSASSSVSYMHWYQQKSGTS<br>PKPWIYEISKLASGVPARFSGSGSGTSYSLTISSMEAEDAAI<br>YYCQQWNYPLYTFGGGTKLEIK |
| 8 | mAb M9A12 Heavy Chain Variable Domain Amino Acid Sequence | FR1-CDR1-FR2-CDR2-FR3-CDR3-FR4<br>EVKLVESGGGLVQPGGSRKLSCAASGFTFSDYGMAWVRQAPG<br>KGPEWVAFISYLAYTVFYADTVTGRFTISRENAKNTLYLEMS<br>SLRSEDTAMYYCSREAYGGGFTYWGQGTLVTV |
| 9 | mAb M9A12 Light Chain Variable Domain Nucleotide Sequence | FR1-CDR1-FR2-CDR2-FR3-CDR3-FR4<br>GAAATTGTGCTCACTCAGTCTCCAGCCATCACAGCTGCATCT<br>CTGGGGCAAAAGGTCACCATCACCTGCAGTGCCAGCTCAAGT<br>GTAAGTTACATGCACTGGTACCAGCAGAAGTCAGGCACCTCC<br>CCCAAACCATGGATTTATGAAATATCCAAACTGGCTTCTGGA<br>GTCCCAGCTCGCTTCAGTGGCAGTGGGTCTGGGACCTCTTAC<br>TCTCTCACAATCAGCAGCATGGAGGCTGAAGATGCTGCCATT<br>TATTACTGCCAGCAGTGGAATTATCCTCTGTACACGTTCGGA<br>GGGGGGACCAAGCTGGAAATAAAA |
| 10 | mAb M9A12 Heavy Chain Variable Domain Nucleotide Sequence | FR1-CDR1-FR2-CDR2-FR3-CDR3-FR4<br>GAGGTGAAGTTGGTGGAGTCTGGGGGAGGCTTAGTGCAGCCT<br>GGAGGGTCCCGGAAACTCTCCTGTGCAGCCTCTGGATTCACT<br>TTCAGTGACTACGGAATGGCGTGGGTTCGACAGGCTCCAGGG<br>AAGGGGCTGAGTGGGTTGCATTCATTAGTTATTTGGCATAT<br>ACTGTCTTCTATGCAGACACTGTGACGGGCCGATTCACCATC<br>TCTAGAGAGAATGCCAAAAACACCCTGTACCTGGAAATGAGC<br>AGTCTGAGGTCTGAGGACACAGCCATGTACTACTGTTCAAGG<br>GAGGCGTACGGGGGAGGGTTTACTTACTGGGGCCAAGGGACT<br>CTGGTCACTGTC |
| 11 | mAb M9A12 Heavy Chain Nucleotide Sequence | Leader sequence-FR1-CDR1-FR2-CDR2-FR3-CDR3-FR4-<u>Constant region</u>-*Stop codon*<br>ATGGACTTCAGGCTCAGCTTACTTATTTTTGTCCTTATTTA<br>AAAGGTGTCCAGTGTGAGGTGAAGTTGGTGGAGTCTGGGGGA<br>GGCTTAGTGCAGCCTGGAGGGTCCCGGAAACTCTCCTGTGCA<br>GCCTCTGGATTCACTTTCAGTGACTACGGAATGGCGTGGGTT<br>CGACAGGCTCCAGGGAAGGGGCCTGAGTGGGTTGCATTCATT<br>AGTTATTTGGCATATACTGTCTTCTATGCAGACACTGTGACG<br>GGCCGATTCACCATCTCTAGAGAGAATGCCAAAAACACCCTG<br>TACCTGGAAATGAGCAGTCTGAGGTCTGAGGACACAGCCATG<br>TACTACTGTTCAAGGGAGGCGTACGGGGGAGGGTTTACTTAC<br>TGGGGCCAAGGGACTCTGGTCACTGT<u>CTCTGCAGCCAAACG<br>ACACCCCCATCGTCTATCCACTGGCCCCTGGATCTGCTGCC<br>CAAACTAACTCCATGGTGACCCTGGGATGCCTGGTCAAGGGC<br>TATTTCCCTGAGCCAGTGACAGTGACCTGGAACTCTGGATCC<br>CTGTCCAGCGGTGTGCACACCTTCCCAGCTGTCCTGCAGTCT<br>GACCTCTACACTCTGAGCAGCTCAGTGACTGTCCCCTCCAGC<br>ACCTGGCCCAGCGAGACCGTCACCTGCAACGTTGCCCACCCG<br>GCCAGCAGCACCAAGGTGGACAAGAAAATTGTGCCCAGGGAT<br>TGTGGTTGTAAGCCTTGCATATGTACAGTCCCAGAAGTATCA</u> |

TABLE B-continued

Sequence listings

| SEQ ID NO: | Description | SEQUENCE |
|---|---|---|
| | | TCTGTCTTCATCTTCCCCCCAAAGCCCAAGGATGTGCTCACC<br>ATTACTCTGACTCCTAAGGTCACGTGTGTTGTGGTAGACATC<br>AGCAAGGATGATCCCGAGGTCCAGTTCAGCTGGTTTGTAGAT<br>GATGTGGAGGTGCACACAGCTCAGACGCAACCCCGGGAGGAG<br>CAGTTCAACAGCACTTTCCGCTCAGTCAGTGAACTTCCCATC<br>ATGCACCAGGACTGGCTCAATGGCAAGGAGTTCAAATGCAGG<br>GTCAACAGTGCAGCTTTCCCTGCCCCATCGAGAAAACCATC<br>TCCAAAACCAAAGGCAGACCGAAGGCTCCACAGGTGTACACC<br>ATTCCACCTCCCAAGGAGCAGATGGCCAAGGATAAAGTCAGT<br>CTGACCTGCATGATAACAGACTTCTTCCCTGAAGACATTACT<br>GTGGAGTGGCAGTGGAATGGGCAGCCAGCGGAGAACTACAAG<br>AACACTCAGCCCATCATGGACACAGATGGCTCTTACTTCGTC<br>TACAGCAAGCTCAATGTGCAGAAGAGCAACTGGGAGGCAGGA<br>AATACTTTCACCTGCTCTGTGTTACATGAGGGCCTGCACAAC<br>CACCATACTGAGAAGAGCCTCTCCCACTCTCCTGGTAAA*TGA* |
| 12 | mAb M9A12 Heavy Chain Amino Acid Sequence | Leader sequence-FR1-CDR1-FR2-CDR2-FR3-CDR3-FR4-Constant region-*Stop codon*<br>MDFRLSLLIFVLILKGVQCEVKLVESGGGLVQPGGSRKLSCA ASGFTFSDYGMAWVRQAPGKGPEWVAFISYLAYTVFYADTVT GRFTISRENAKNTLYLEMSSLRSEDTAMYYCSREAYGGGFTY WGQGTLVTVSAAKTTPPSVYPLAPGSAAQTNSMVTLGCLVKG YFPEPVTVTWNSGSLSSGVHTFPAVLQSDLYTLSSSVTVPSS TWPSETVTCNVAHPASSTKVDKKIVPRDCGCKPCICTVPEVS SVFIFPPKPKDVLTITLTPKVTCVVVDISKDDPEVQFSWFVD DVEVHTAQTQPREEQFNSTFRSVSELPIMHQDWLNGKEFKCR VNSAAFPAPIEKTISKTKGRPKAPQVYTIPPPKEQMAKDKVS LTCMITDFFPEDITVEWQWNGQPAENYKNTQPIMDTDGSYFV YSKLNVQKSNWEAGNTFTCSVLHEGLHNHHTEKSLSHSPGK- |
| 13 | mAb M9A12 Light Chain Nucleotide Sequence | Leader sequence-FR1-CDR1-FR2-CDR2-FR3-CDR3-FR4-Constant region-*Stop codon*<br>ATGGACTTTCGGGTGCAGATTTTCAGCTTCCTGCTAATCAGT GTCACAGTGTCCAGAGGAGAAATTGTGCTCACTCAGTCTCCA GCCATCACAGCTGCATCTCTGGGGCAAAAGGTCACCATCACC TGCAGTGCCAGCTCAAGTGTAAGTTACATGCACTGGTACCAG CAGAAGTCAGGCACCTCCCCCAAACCATGGATTTATGAAATA TCCAAACTGGCTTCTGGAGTCCCAGCTCGCTTCAGTGGCAGT GGGTCTGGGACCTCTTACTCTCTCACAATCAGCAGCATGGAG GCTGAAGATGCTGCCATTTATTACTGCCAGCAGTGGAATTAT CCTCTGTACACGTTCGGAGGGGGGACCAAGCTGGAAATAAAA CGGGCTGATGCTGCACCAACTGTATCCATCTTCCCACCATCC AGTGAGCAGTTAACATCTGGAGGTGCCTCAGTCGTGTGCTTC TTGAACAACTTCTACCCCAAAGACATCAATGTCAAGTGGAAG ATTGATGGCAGTGAACGACAAAATGGCGTCCTGAACAGTTGG ACTGATCAGGACAGCAAAGACAGCACCTACAGCATGAGCAGC ACCCTCACGTTGACCAAGGACGAGTATGAACGACATAACAGC TATACCTGTGAGGCCACTCACAAGACATCAACTTCACCCATT GTCTAGAAGAGCTTCAACAGGAATGAGTGT*TAG* |
| 14 | mAb M9A12 Light Chain Amino Acid Sequence | Leader sequence-FR1-CDR1-FR2-CDR2-FR3-CDR3-FR4-Constant region-*Stop codon*<br>MDFRVQIFSFLLISVTVSRGEIVLTQSPAITAASLGQKVTIT CSASSSVSYMHWYQQKSGTSPKPWIYEISKLASGVPARFSGS GSGTSYSLTISSMEAEDAAIYYCQQWNYPLYTFGGGTKLEIK RADAAPTVSIFPPSSEQLTSGGASVVCFLNNFYPKDINVKWK IDGSERQNGVLNSWTDQDSKDSTYSMSSTLTLTKDEYERHNS YTCEATHKTSTSPIVKSFNRNEC- |

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Identification of the Novel Tumor Specific Biomarker and Generation of Monoclonal Antibody M9A12

In the development of serum diagnostic assays, it is essential to identify tumor specific biomarkers and create ligands such as antibodies that can bind to the biomarkers. Glycans serve a variety of structural and functional roles in cell surface and secreted proteins. Glycosylation changes are a universal feature of malignant transformation and tumor progression. The inventors identified a group of tumor specific biomarkers, tumor associated complex N-glycans with terminal GlcNAcβ residues. The newly discovered tumor antigens, tumor associated complex N-glycans with terminal GlcNAcβ residues, are specifically expressed on the surfaces of different types of cancer cells (FIG. 1). The group of tumor associated complex N-glycans were detected on cultured living ovarian cancer cells, colon cancer cells, pancreatic cancer cells, and lung cancer cells.

Figure 2:
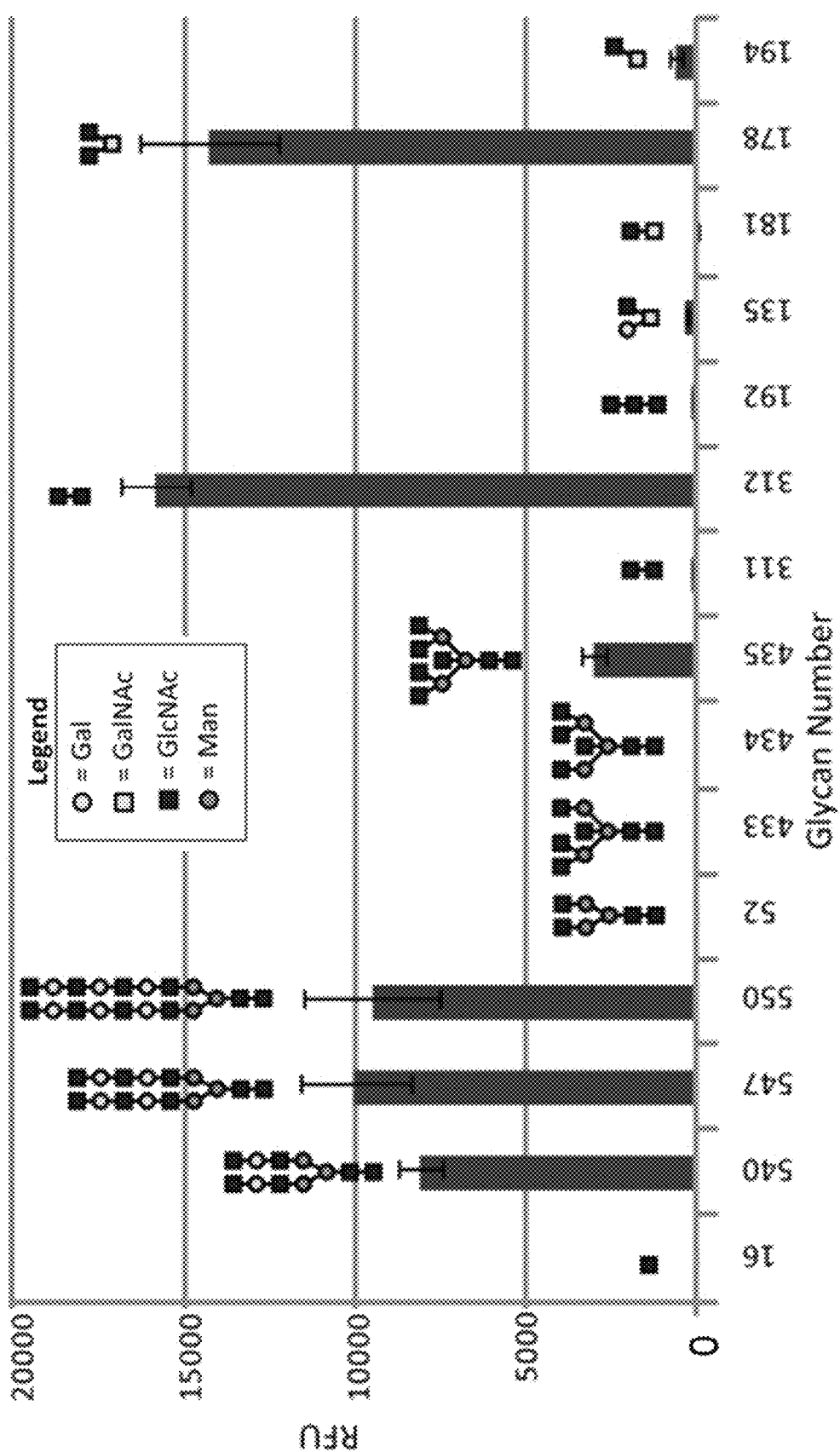
FIG. 2 depicts a graph showing the binding of mAb M9A12 to selected carbohydrates on the CFG (Consortium for Function Glycomics) glycan array (version 5). A cartoon representation of each glycan is shown above the bars. Error bars correspond to the standard deviation between replicate spots on an array slide. The x-axis lists the glycan ID number on the CFG array. The y-axis is relative fluorescence units (RFU).

Using a hybridoma technique, the inventors successfully generated mAb M9A12 to tumor associated complex N-glycans with terminal GlcNAcβ residues. This antibody was classified as an IgG1 immunoglobulin subclass with a significant binding affinity (Kd>2×10$^9$) to the antigens. Using the Consortium of Functional Glycomics (CFG) glycan array (version 5) (www.functionalglycomics.org/static/consortium/resources/resourcecoreh16.shtml), the binding site of mAb M9A12 was analyzed. It was determined that mAb M9A12 binds to tumor associated complex N-glycans with terminal GlcNAcβ residues. FIG. 2 and Table 1 depict glycans that are specifically bound by mAb M9A12. The results in FIG. 2 and Table 1 imply that other features of presentation, such as the protein core, spacing, and orientation of the N-glycans, may also influence the binding, and it further confirms that mAb M9A12 and its binding antigens are unique and novel.

human pancreatic cancer tissues demonstrates specific binding of mAb M9A12 to cancer tissues and shows the location of the tumor associated complex N-glycans in the lumens of cancerous glandular structures, on tumor cell membranes and in the areas of Golgi complex in the cytoplasm (FIG. 5), indicating that the tumor associated complex N-glycans with terminal GlcNAcβ residues are secreted antigens which favor the development of biofluid based assays for cancer detection and diagnosis. In lung cancer, the positive staining rate of mAb M9A12 is about 85.5% with significant specificity (FIG. 8). Adenocarcinoma, squamous carcinoma and small cell carcinoma of the lung all show positive staining. Normal lung tissue and chronic bronchitis tissue demonstrate negative staining. Chronic bronchitis with epithelial hyperplasia exhibit positive staining in the areas of Golgi complex.

Next, an exosome bound tumor associated complex N-glycan based ELISA assay for efficiently measuring the tumor associated complex N-glycans with terminal GlcNAcβ residues in biofluid was developed. There are at least three major advantages of measuring the exosome bound tumor associated complex N-glycans for cancer detection and diagnosis. First, the tumor associated complex N-glycans can be co-isolated with exosomes. The exosome bound tumor associated complex N-glycans, unlike soluble tumor associated antigens which are much more diluted after secretion from tumor cells into a large blood pool, can be

TABLE 1

Binding sites analysis of mAb M9A12 with Glycan array (Version 5), Protein-Glycan Interaction Core (H) of The Consortium for Functional Glycomics.

| ID No | Glycan Structure |
|---|---|
| 16 | GlcNAcβ-Sp0 |
| 52 | GlcNAcβ1-2Mana1-6(GlcNAcb1-2Mana1-3)Manb1-4GlcNAcb1-4GlcNAcb-Sp12 |
| 135 | GlcNAcβ1-6(Galb1-3)GalNAca-Sp14 |
| 178* | GlcNAcβ1-6(GlcNAcb1-3)GalNAca-Sp14 |
| 181 | GlcNAcβ1-3GalNAca-Sp14 |
| 192 | GlcNAcβ1-6GalNAca-Sp8 |
| 194 | GlcNAcβ1-6GalNAca-Sp14 |
| 311 | GlcNAcβ1-4GlcNAcβ-Sp10 |
| 312* | GlcNAcβ1-4GlcNAcβ-Sp12 |
| 433 | GlcNAcβ1-2Mana1-6(GlcNAcb1-4)(GlcNAcb1-4(GlcNAcb1-2)Mana1-3)Manb1-4GlcNAcb1-4GlcNAc-Sp21 |
| 434 | GlcNAcβ1-6(GlcNAcb1-2)Mana1-6(GlcNAcb1-4)(GlcNAcb1-2Mana1-3)Manb1-4GlcNAcb1-4GlcNAc-Sp21 |
| 435* | GlcNAcβ1-6(GlcNAcb1-2)Mana1-6(GlcNAcb1-4)(GlcNAcb1-4(GlcNAcb1-2)Mana1-3)Manb1-4GlcNAcb1-4GlcNAc-Sp21 |
| 540* | GlcNAcβ1-3Galb1-4GlcNAcb1-2Mana1-6(GlcNAcb1-3Galb1-4GlcNAcb1-2Mana1-3)Manb1-4GlcNAcb1-4GlcNAcb-Sp12 |
| 547* | GlcNAcβ1-3Galb1-4GlcNAcb1-3Galb1-4GlcNAcb1-2Mana1-6(GlcNAcb1-3Galb1-4GlcNAcb1-3Galb1-4GlcNAcb1-2Mana1-3)Manb1-4GlcNAcb1-4GlcNAcb-Sp25 |
| 550* | GlcNAcβ1-3Galb1-4GlcNAcb1-3Galb1-4GlcNAcb1-3Galb1-4GlcNAcb1-2Mana1-6(GlcNAcb1-3Galb1-4GlcNAcb1-3Galb1-4GlcNAcb1-3Galb1-4GlcNAcb1-2Mana1-3)Manb1-4GlcNAcb1-4GlcNAcb-Sp25 |

GlcNAcβ Glycans with * on ID # are binders for mAb M9A12. Glycans with GlcNAcβ determinants without star labeling are non-binders of mAb M9A12 (See FIG. 2).

Figure 3:
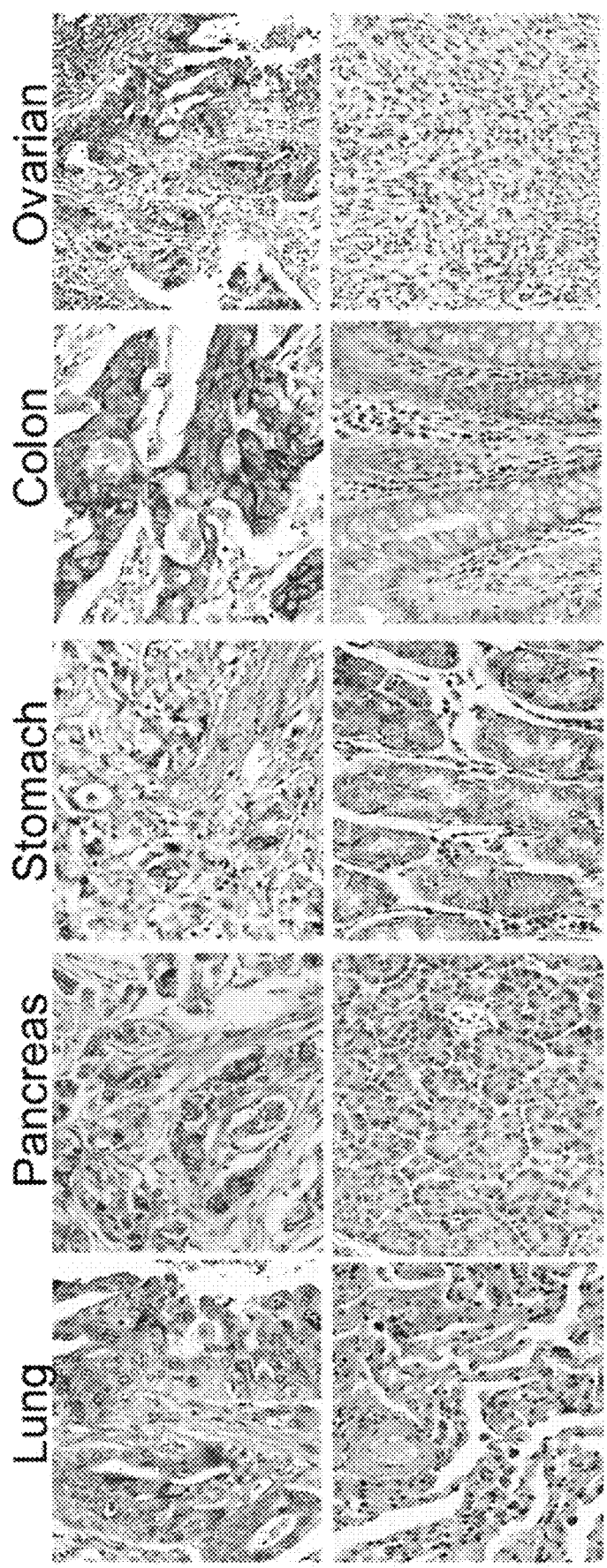
FIG. 3 depicts immunohistochemical staining of mAb M9A12 in human cancer tissues and their normal counter parts. It shows intensive staining of mAb M9A12 in lung, pancreatic, stomach, colon and ovarian cancer tissues (upper panels). In contrast, mAb M9A12 did not stain their normal counter parts (lower panels) except very weak staining in a few epithelial cells of colon and stomach mucosa.
Figure 4:
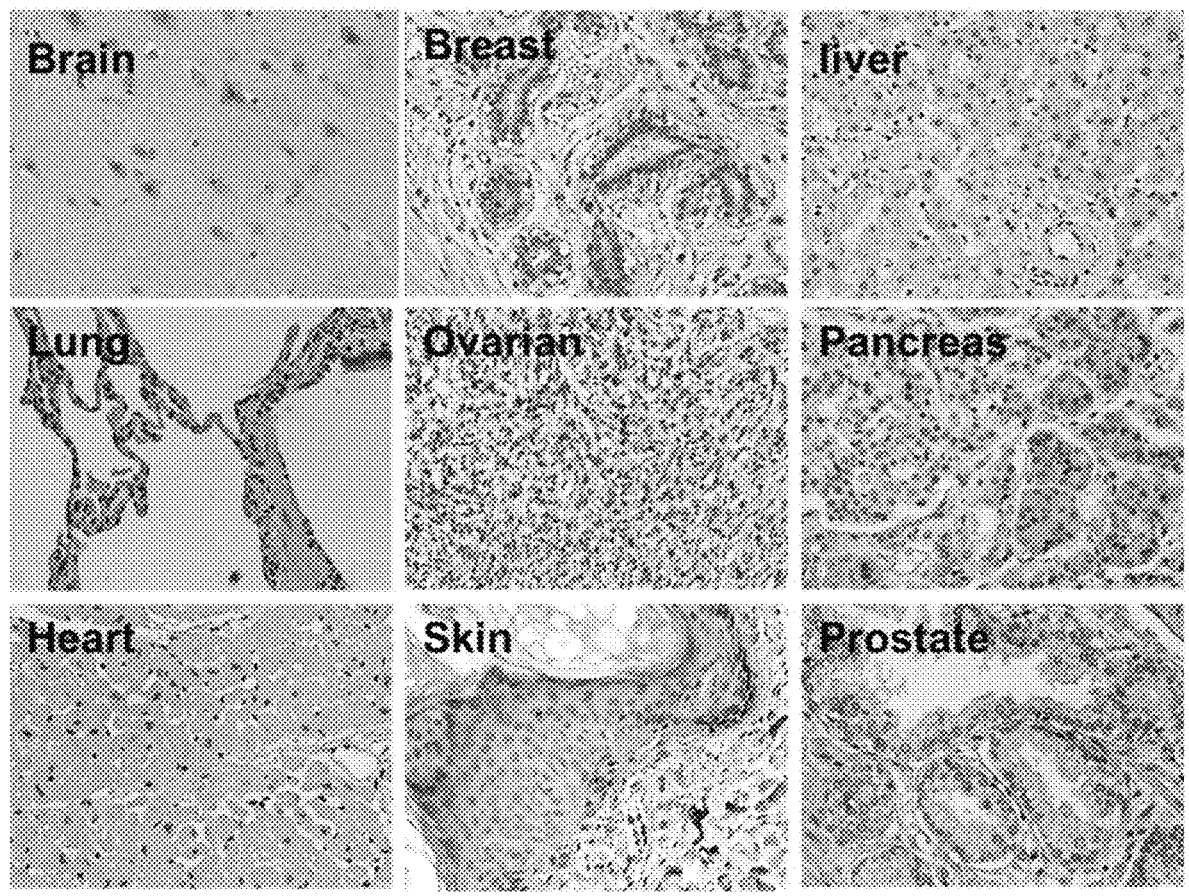
FIG. 4 depicts immunohistochemical staining of mAb M9A12 in human normal tissues (Tissue array, BN 243, Biomax. US). mAb M9A12 binding of tumor associated complex N-glycans was not detected in human normal cells and tissues.
Figure 9:
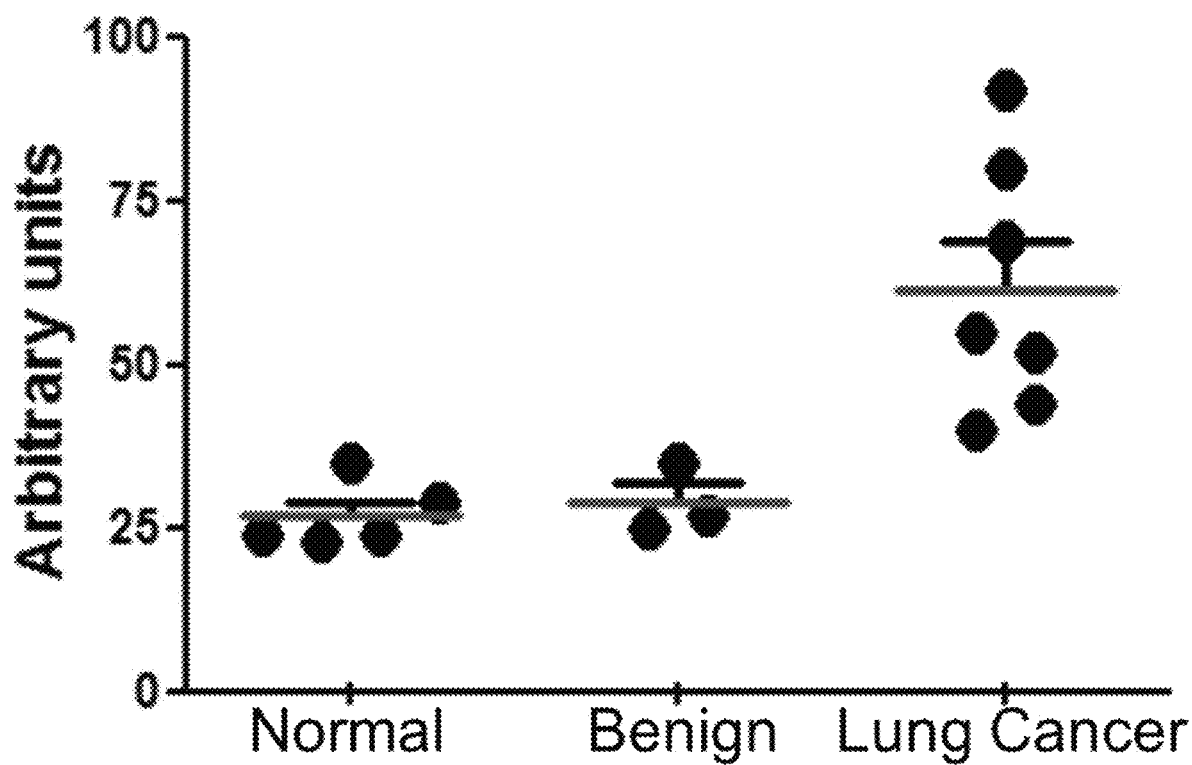
FIG. 9 depicts an ExoELISA assay of mAb M9A12 in the measurement of exosome bound complex N-glycans with terminal GlcNAcβ residues in serum from healthy individuals and patients with lung benign and malignant diseases. The median arbitrary units are 27, 29 and 65.4 in healthy individuals and patients with lung benign disease and cancer (red bars). The differences between normal/benign control groups and cancer group are statistically significant (P<0.005).
Figure 11:
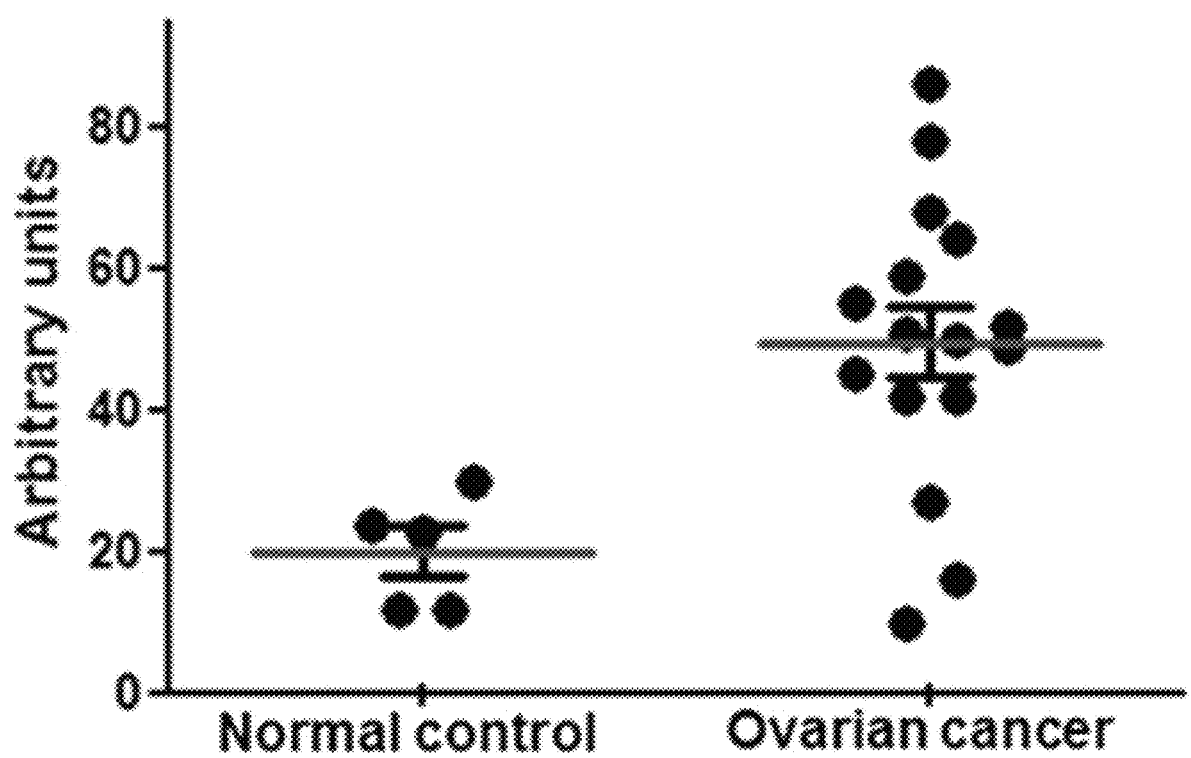
FIG. 11 depicts an ExoELISA assay of mAb M9A12 in the measurement of exosome bound complex N-glycans with terminal GlcNAcβ residues in sera from healthy individuals and patients with ovarian cancer. The median arbitrary units are 17.1 and 50.6 in healthy individuals and patients with ovarian cancer, respectively (red bars). The difference between normal control and cancer groups is statistically significant (P<0.005). 81% of ovarian cancer patients (13/16 cases) are positive if we set the cut off value at 35 arbitrary units. In contrast, 100% of normal control (5/5 cases) is below the cut off value (negative).
Figure 12:
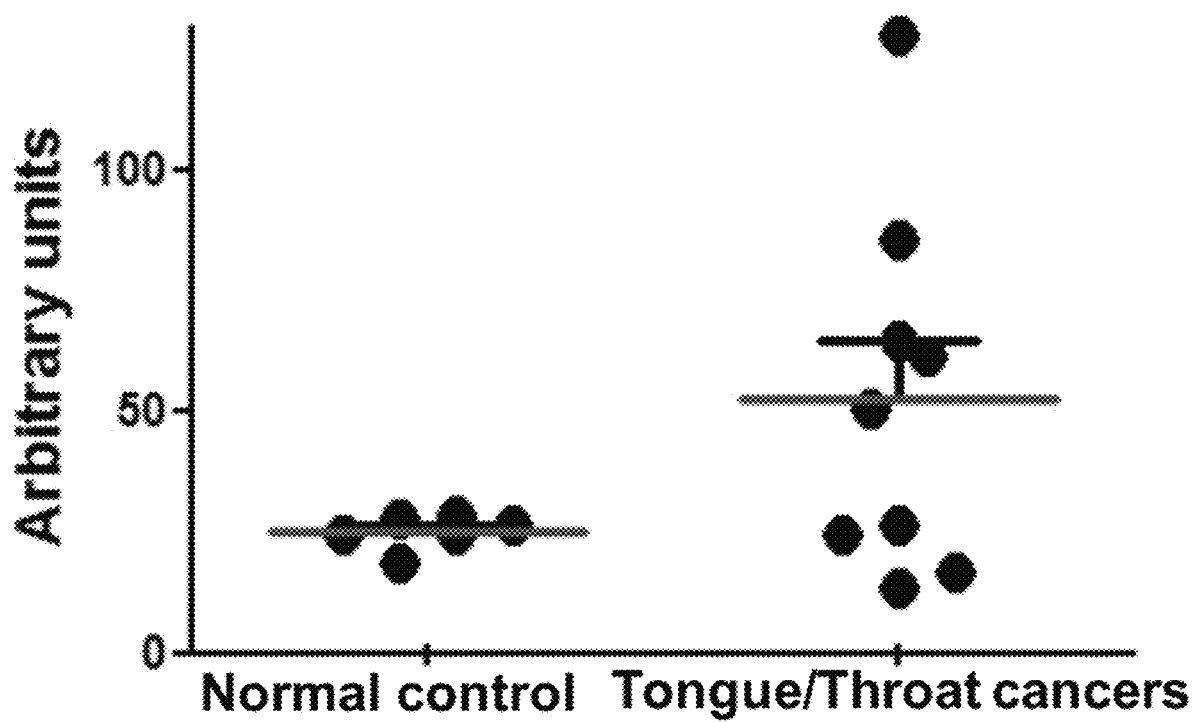
FIG. 12 depicts an ExoELISA assay of mAb M9A12 in the measurement of exosome bound complex N-glycans with terminal GlcNAcβ residues in sera from healthy individuals and patients with tongue/pharynx/larynx cancers. The median arbitrary units are 25.3 and 52 in healthy individuals and patients with tongue/pharynx/larynx cancers respectively (red bars). The difference between normal control and cancer groups is statistically significant (P<0.005). However, about 40% of patients with tongue/pharynx/larynx cancers shows false negative results.

Using immunohistochemical (IHC) staining, it was the specificity of mAb M9A12 for cancer cells versus normal counterparts was confirmed. Intensive staining was observed in lung, pancreatic, stomach, colon and ovarian cancer tissues relative to their normal counterparts (FIG. 3). Additional IHC of human normal cells and tissues using mAb M9A12 revealed that tumor associated complex N-glycans B were not detected in normal brain, breast, liver, lung, ovarian, pancreas, heart, skin or prostate tissue (FIG. 4). In pancreatic cancer, the positive staining rate of mAb M9A12 is about 98% (105/107). IHC staining using mAb M9A12 in easily enriched and isolated from biofluid. This enrichment can improve the sensitivity of cancer detection and diagnosis. Second, tumor cells release greater quantities of exosomes than normal cells. Approximately each tumor cell can release >5,000 exosomes in a 24 hour period. So, measuring the exosome bound tumor associated complex N-glycans or tumor associated complex N-glycan positive exosomes is more sensitive than searching for tumor cells in circulation for cancer detection and diagnosis. Third, measuring the biofluid exosome bound antigens for cancer detection and diagnosis is non-invasive, economical and easy to perform in the clinic. Presently, the exosome bound tumor associated complex N-glycans in serum from healthy individuals and patients with benign and malignant diseases was measured. The results clearly demonstrate that cancer patients can be distinguished from healthy individuals and patients with benign diseases by measuring the serum exosome bound tumor associated complex N-glycans with terminal GlcNAcβ residues. In healthy individuals and patients with ovarian cancer, the mean arbitrary units using the exosome based ELISA assay (ExoELISA assay) are 17.1 and 50.6 respectively. Using a cut off value at 35 arbitrary units, 81% of ovarian cancer patients are positive and 100% of healthy individuals are negative (FIG. 11). The ExoELISA assay was also used to measure the exosome bound tumor associated complex N-glycans in the serum from healthy individuals and patients with lung benign and malignant diseases. The median arbitrary units are 37, 29 and 65.4, respectively (FIG. 9). In healthy individuals and patients with tongue/pharynx/larynx cancer, the mean arbitrary units are 25.3 and 52, respectively (FIG. 12).

Example 2. Discovery of the Novel Tumor Specific Complex N-Glycans with Terminal GlcNAcβ Residues Provides an Ideal Biomarkers for Development of Assays for Pancreatic Cancer Detection and Diagnosis Pancreatic adenocarcinoma is a disease with dismal prognoses. The poor prognosis can be contributed to the following factors: 1) silent nature of the disease and late diagnosis (only ~20% of cases present as resectable disease at the time of diagnosis); 2) high metastatic potential and resistance to conventional chemotherapy and radiotherapy; 3) lack of methods for accurately measuring patient response to therapeutic treatment. Currently, surgical resection is the only curative treatment for patients with pancreatic cancer. However, nearly 80% of patients at the time of diagnosis are not surgical candidates due to tumor vasculature involvements or the presence of metastatic spread. Even in patients with curative resection, the median survival is less than two years. Studies have shown that patients with early stage pancreatic lesions (<3 cm) without lymphatic invasion have a significantly better prognosis with a 5-year survival rate of up to 25-30% following surgical resection, illuminating the importance of early detection and diagnosis. Thus, in order to reduce mortality and improve prognosis, it is essential to develop noninvasive and economical assays for early pancreatic cancer detection, assessment of therapeutic response and monitoring of tumor recurrence. Unfortunately, no serum based assays are presently available for early pancreatic cancer detection and diagnosis.

Figure 5:
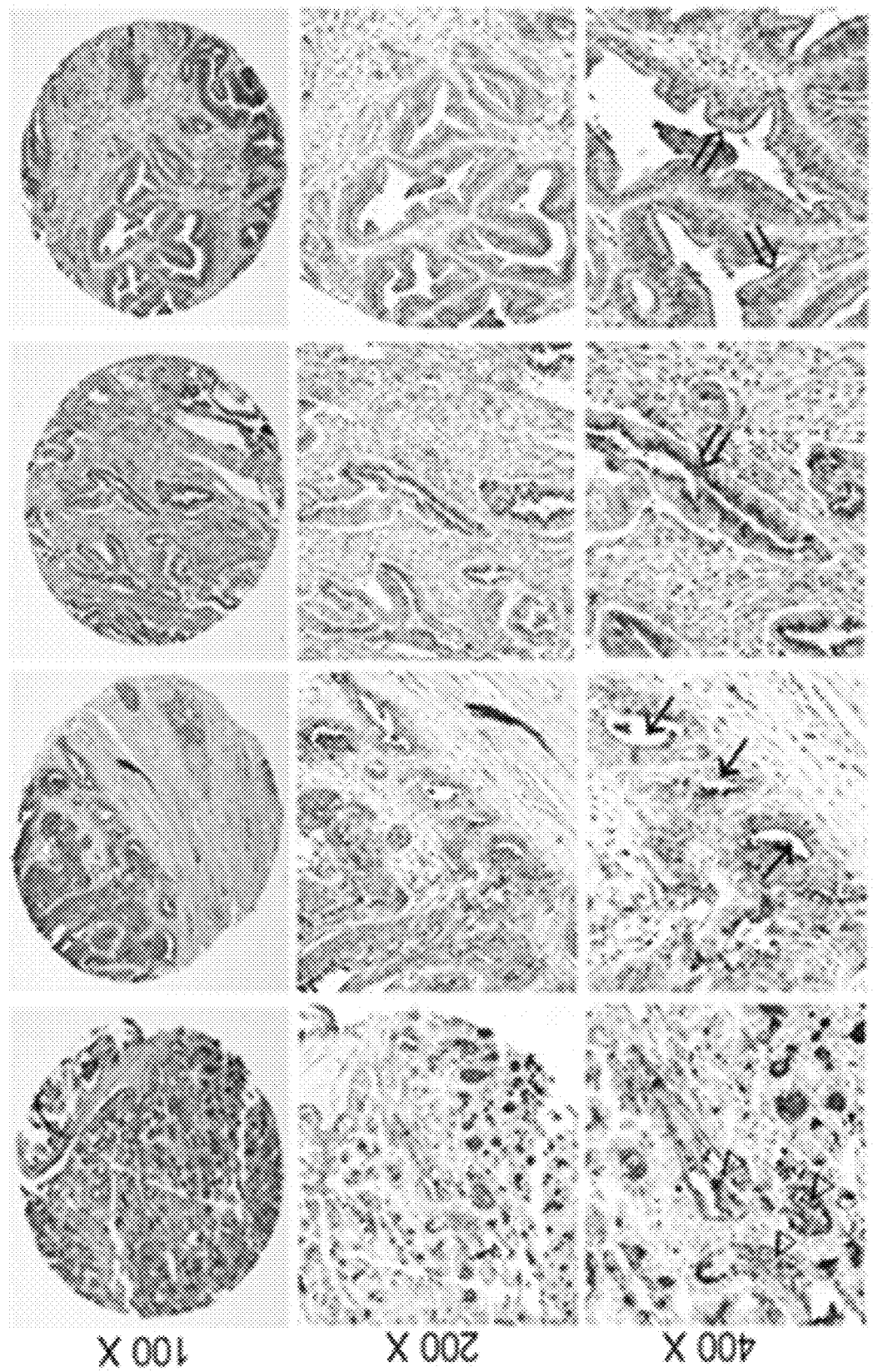
FIG. 5 depicts immunohistochemical staining of mAb M9A12 in human pancreatic cancer tissues. This figure demonstrates specific binding of mAb M9A12 to cancer tissues and shows the location of the complex N-glycans in the lumens of cancerous glandular structures (arrows), on tumor cell membranes (arrow heads) and in the areas of Golgi complex in the cytoplasm (open arrows).
Figure 6:
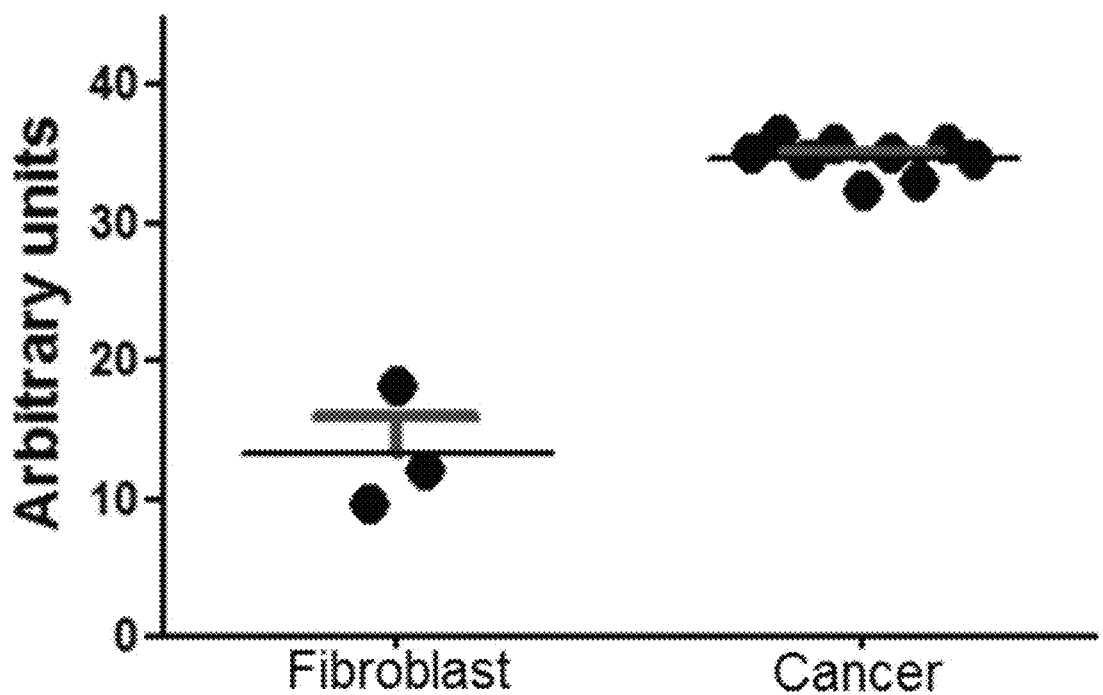
FIG. 6 depicts an ExoELISA assay of mAb M9A12 in the measurement of exosome bound complex N-glycans with terminal GlcNAcβ residues in the supernatant of pancreatic cancer and fibroblast cell cultures. Pancreatic cancer cell lines are, SW-1990, Mia-PaCa-2, 293TV, HPAC, HS766T, PANC-1, CFPAC-1, MPAC-1 and Capan-1. Culture supernatants of fibroblasts are from human momentum tissue primary culture. The average arbitrary unites between fibroblast and cancer are significantly different (P=0.007).

As described in Example 1, the tumor specific biomarkers, complex N-glycans with terminal GlcNAcβ residues, were identified and mAb M9A12 to the tumor associated complex N-glycans was successfully generated. This antibody was classified as an IgG1 immunoglobulin subclass with a significant binding affinity (Kd>2×10$^9$) to the antigen. The antibody stained plasma membranes of cultured pancreatic cancer cells is shown in FIG. 1C. The group of tumor associated complex N-glycans with terminal GlcNAcβ residues has not previously been reported as tumor associated antigens. As demonstrated in FIG. 1C, cultured human pancreatic cancer cells (Panc-1) stained intensively with mAb M9A12 in the cell membranes. mAb M9A12 displayed significant tumor specificity (FIG. 5 and FIG. 4). The positive staining rate with mAb M9A12 in pancreatic cancer is about 98% (105/107) [negative (−) 1.9% (2/107); weak positive (±) 18.7% (20/107); positive (+) 39.3% (42/107); strong positive (++) 31.8% (34/107); and very strong positive (+++) 8.4% (9/107)] (FIG. 5). Accordingly, the tumor associated complex N-glycans with terminal GlcNAcβ residues which have excellent tumor specificity and sensitivity are ideal candidate biomarkers for development of assays for pancreatic cancer detection and diagnosis.

Example 3. ExoELISA Assay for Pancreatic Cancer Detection and Diagnosis

Figure 7:
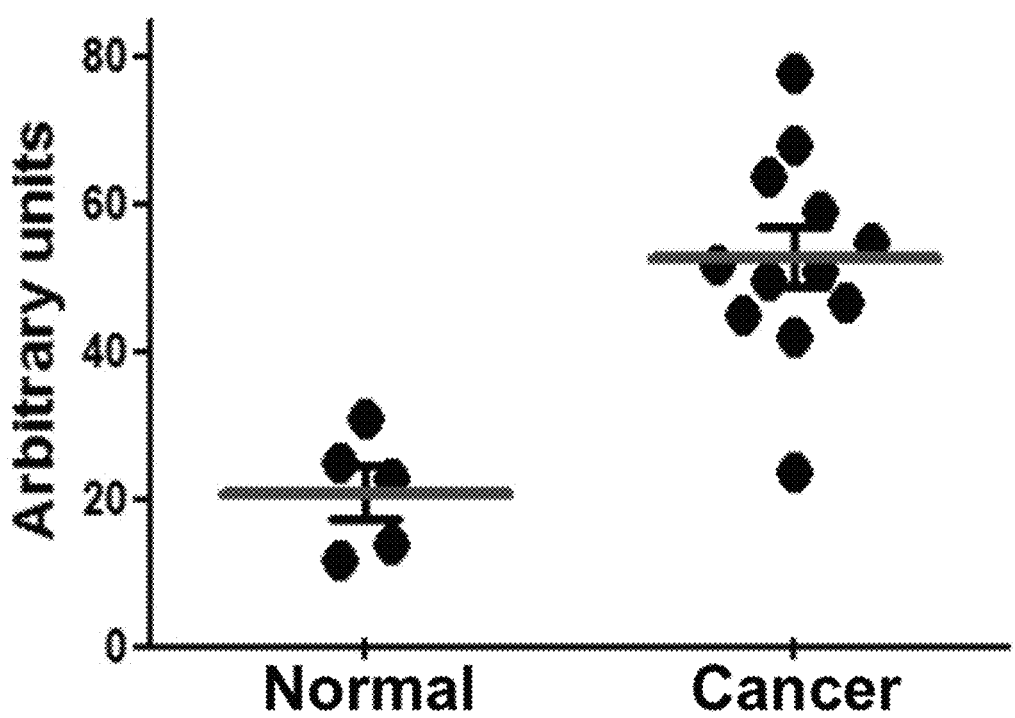
FIG. 7 depicts an ExoELISA assay of mAb M9A12 in the measurement of exosome bound complex N-glycans with terminal GlcNAcβ residues in sera from healthy individuals and patients with pancreatic cancer. The median arbitrary units are 21 and 53 in healthy individuals and patients with pancreatic cancer, respectively (red bars). The difference between normal control and cancer groups is statistically significant (P<0.05).
Figure 8A:
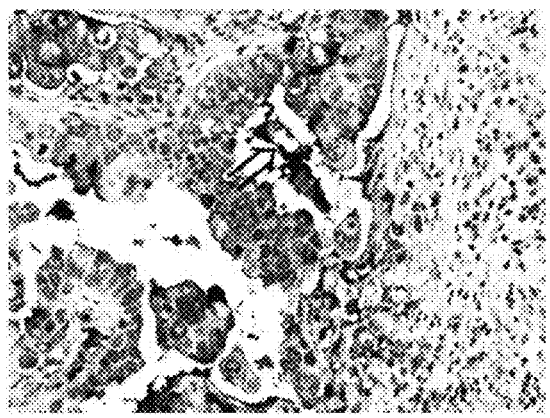
FIG. 8A, FIG. 8B, FIG. 8C, FIG. 8D, FIG. 8E and FIG. 8F depict immunohistochemical staining of mAb M9A12 in lung normal, benign and malignant tissues.
Figure 8B:
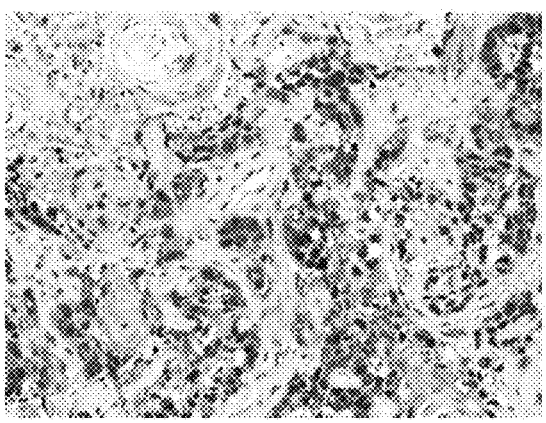
Figure 8C:
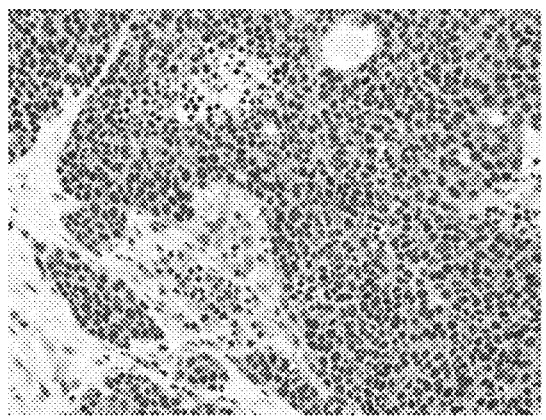
Figure 8D:
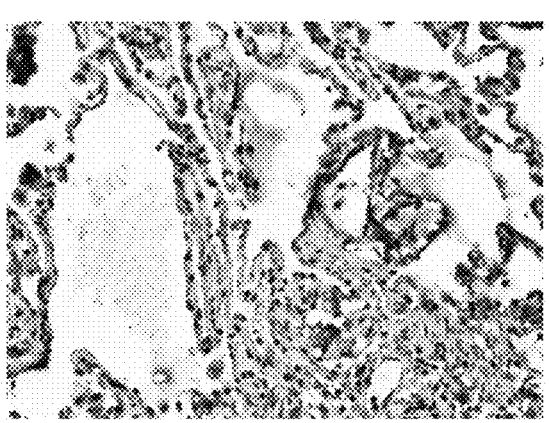
Figure 8E:
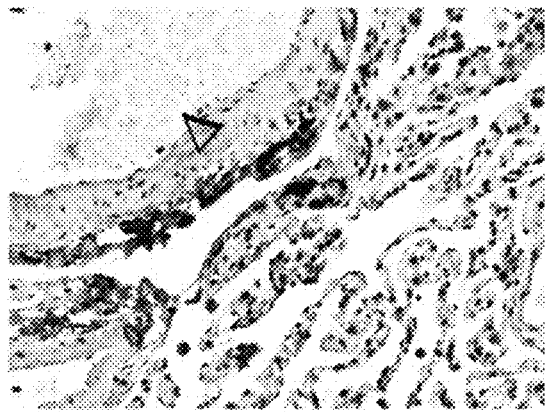
Figure 8F:
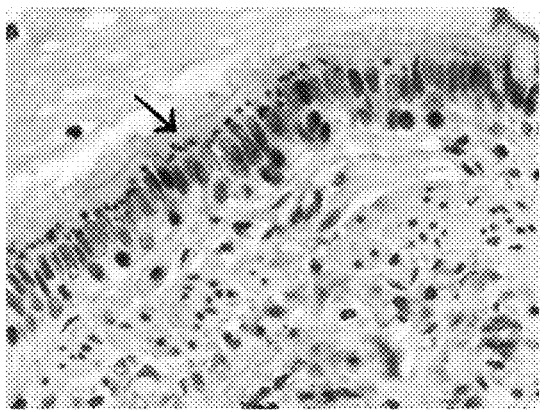

One of the major problems in cancer serum diagnosis is the insufficient sensitivity of blood tests due to a low-abundance of tumor associated antigens in serum. For instance, the ratio of prostate specific antigen to albumin in serum is 1 to 7.5 million molecules. Detecting a tumor specific molecule is like searching for a needle in a haystack. Exosomes have recently become a point of focus in efforts to identify biomarkers for the purpose of diagnosis. Exosomes are 30- to 100-nm, lipid bilayer membrane-bound vesicles that are released by most types of cells, including tumor cells. Exosomes express molecular markers that are generally linked with tumor plasma membranes, and they carry both genomic and proteomic materials such as proteins, miRNA, lipids, glycans and DNA of the cells from which they were derived. Studies have shown that some exosome miRNAs can be used as diagnostic and prognostic markers. Lately, exosome membrane bound tumor markers have been explored. Presently, serum exosome membrane proteins and carbohydrate antigens have not yet been intensively evaluated in cancer, particularly in pancreatic cancer. The exosome bound tumor associated complex N-glycans were recovered from serum with elevated levels in pancreatic cancer patients (FIG. 7). The exosome bound tumor associated complex N-glycans, unlike soluble tumor associated antigens which are much more diluted after secretion from tumor cells into a large blood pool, can be easily enriched and isolated from body fluid. In addition, tumor cells release much more exosomes than normal cells. Approximately each tumor cell can release more than 5,000 exosomes in a 24 hour period. Measuring the tumor circulating exosome bound tumor associated complex N-glycans with terminal GlcNAcβ residues or the tumor associated complex N-glycan positive exosomes could be more sensitive than searching for tumor cells in circulation for cancer detection and diagnosis. An ExoELISA assay has been established which measures the exosome bound tumor associated complex N-glycans. The ExoELISA assay has demonstrated promising results for pancreatic cancer detection and diagnosis in a small trial. The ExoELISA assay could be able to differentiate pancreatic cancer patients from normal individuals and patients with benign pancreatic diseases, and could serve as a noninvasive and economical tool for early pancreatic cancer detection. Additionally, the ExoELISA assay could be used to develop a kit for early pancreatic cancer detection and diagnosis, and for accurately monitoring disease progression and therapeutic response.

Preparation of mAb M9A12 for Measuring the Serum Exosome Bound Tumor Associated Complex N-Glycans in Normal Individuals and Patients with Malignant and Benign Disease:

mAb M9A12 will be produced by collecting hybridoma culture medium and purifying it using protein A/G Sepharose beads following the procedures routinely used in our laboratory. Briefly, the supernatant from the M9A12 hybridoma culture will be collected and centrifuged at 14,000×g for 20 min at 4° C., filtered through a 0.22 μm filter to remove fine particles, and the pH will be adjusted to 7.0 using equilibration buffer (1 mol/L Tris, pH 9.0). The filtered supernatant will be passed through a protein A/G column and the column will be washed with binding buffer (50 mmol/L Na2PO4, 500 mmol/L NaCl, pH 6) before eluting the antibody from the column with glycine buffer (0.1 mol/L, pH 2.7). The eluent containing antibody will be collected in a test tube enclosing 100 μL of Tris buffer (1 mol/L, pH 9.0) for neutralization, quantifying it with Nanodrop at 280 nm wavelength and store it in a −20° C. freezer for future use.

Experimental Grouping and the Criteria for Enrollment of Patients:

Three groups will be set up: normal control group, pancreatic cancer group and benign pancreas condition group, with 60 cases in each group. Based on the literature and our calculations, this design will give adequate power to estimate the AUC [areas under the ROC (Receiver Operating Characteristic) curve] of mAb M9A12 in pancreatic cancer diagnoses. For the normal control group, 60 healthy volunteers will randomly be recruited. For the pancreatic cancer group, only patients with pancreatic cancer who have not received any treatment are eligible for enrollment. The benign pancreatic disease group will include patients with chronic pancreatitis, pancreatic cysts, intraductal papillary mucinous neoplasm (IPMN), and benign biliary obstruction in which serum CA19-9 is high and gives false positive results when measuring CA19-9 antigen for pancreatic cancer detection. All serum sample collection will be conducted under an Institutional Review Board (IRB) approval.

Enrichment and Isolation of Exosome from Serum:

Exosomes will be enriched from patient serum using a serum exosome isolation kit (Life technology, Cat3 4478360) following the manufacturer's instructions. Briefly, the protocol includes: 1) centrifuge a 0.6 ml serum sample at 2,000 RPM for 30 minutes to remove cells and debris; 2) transfer the clarified serum to a new tube without disturbing the pellet, and place it on ice until ready to perform the isolation; 3) add 100 plexosome isolation reagent to the 0.5 ml serum and mix it well by vortexing; 4) incubate the sample at 2° C. to 8° C. for 30 minutes; 5) centrifuge the sample at 10,000×g for 10 minutes at room temperature after incubation; 6) aspirate and discard the supernatant—exosomes are contained in the pellet at the bottom of the tube; 7) add 150 μl 1× phosphate buffered saline (PBS), suspend the pellet, and finally store the exosome at −80° C. for future use or use it immediately in the ExoELISA assay.

ExoELISA Assay for Quantitatively Measuring the Serum Exosome Bound Tumor Associated Complex N-Glycans:

A pan exosome capture immunoplate precoated with exosome specific rabbit polyclonal antibodies (produced by HansaBiomed and distributed by Galen Laboratory Supplies, Middletown, Conn.) will be used. The concentration of isolated exosomes was previously optimized for the immunoplate maximal capture by serial dilution of isolated exosomes from the sera of normal individuals and pancreatic cancer patients. Results indicated that the immunoplate was saturated for a maximal capturing of exosomes using 50 μl of exosome suspension prepared from the exosome isolated from 0.5 ml serum and resolved in 150 μl of PBS. For measuring the exosome bound tumor associated complex N-glycans, the ExoELISA assay will be performed according to the manufacturer's instructions. Briefly, 1). add 50 μl of concentrated or isolated serum exosome samples into each well and triplicate for each sample; 2). seal the plate with parafilm and incubate at 4° C. overnight or room temperature for 2 hours with gentle shaking; 3). wash the plate three times by adding 200 μl of washing buffer (PBS+0.05% of tween20 and 0.5% of BSA) and discard plate contents by pouring out. 4). add 100 μl M9A12 antibody at a concentration of 10 μg/ml—this is the antibody concentration used for immunohistochemical staining on histo-pathological slides. 5). incubate the plate at room temperature for 1 hour; 6). add 100 μl of goat anti-mouse IgG secondary antibody conjugated with Fluor 488 fluorescent dye (500× dilution) after washing and incubate the plate at room temperature for 1 hour. 7). finally read the plate using a Synergy H1 Hybrid Multi-Mode Microplate Reader with area scan program and an excitation/emission wavelength of 485 nm and 528 nm after washing the plate three times with washing buffer. To quantify the serum exosome bound tumor associated complex N-glycans, a quantitative standard curve will be generated by parallel running carbohydrate binding plates precoated with hydrazide groups which are able to covalently bind carbohydrate groups (Carbo-BIND™, Costar 2507) with the ExoELISA assay using different concentration of pure complex N-glycans with terminal GlcNAcβ residues (V-LABS, INC. Covington, La.). Pure complex N-glycans with terminal GlcNAcβ residues (weigh ratio for different types of glycans is 1:1) will be serially diluted from 1 ng/ml to 100 μg/ml, Nevertheless, the tumor associated complex N-glycan concentration will be adjusted according to the amount of the exosome bound tumor associated complex N-glycans in serum from patients with pancreatic cancer. All experiments will be repeated three times. The average amount (nanogram or microgram) of serum exosome bound tumor associated complex N-glycans will be analyzed. A parallel CA19-9 ELISA assay will also be run with the tumor associated complex N-glycan ExoELISA assay using the same set of serum samples. The serum exosome bound tumor associated complex N-glycans will be validated in the diagnosis of pancreatic cancer by (1) comparing the mean values of the tumor associated complex N-glycan amount and/or fluorescence intensity (arbitrary unit) of pancreatic cancer group to those of the normal control and benign pancreas condition groups statistically using the ANOVA and two-sample student t test, and (2) comparing the sensitivity and specificity of the serum exosome bound tumor associated complex N-glycans in pancreatic cancer diagnosis to CA19-9 with the analyses of a Receiver Operating Characteristic (ROC) Curve. Finally, to determine if the combination of exosome bound tumor associated complex N-glycans and CA19-9 can improve the performance of pancreatic cancer diagnosis by comparing AUCs derived from tumor associated complex N-glycans alone, CA19-9 alone, the combination of the tumor associated complex N-glycans and CA19-9, and a null AUC of 0.5 using Delong's method. CEA as an additional biomarker will also be evaluated.

Example 4. Correlation Between the Amount of Serum Exosome Bound Tumor Associated Complex N-Glycans with Terminal GlcNAcβ Residues and Tumor Burden (Mass)

The serum exosome bound tumor associated complex N-glycans will be measured in pancreatic cancer patients before and after resection of tumors to build a correlation between the amount of the serum exosome bound tumor associated complex N-glycans and tumor burden. CA19-9 will also be measured in the same set of samples and compare the tumor-marker associations between the serum exosome bound tumor associated complex N-glycans and CA19-9. The ExoELISA assay described in Example 3 may lead to mass screening for pancreatic cancer early detection and diagnosis. However, to monitor disease progression and therapeutic response, the serum exosome bound tumor associated complex N-glycans will be measured in 30 patients with advanced (stage III and IV) pancreatic cancer before and after partial or total tumor removal using the same methods as described in Example 3. This sample size of 30 patients gives a power of >0.8 in a paired t-test at a 2-sided 0.05 significance level. Note that serum specimens will be collected and the exosome bound tumor associated complex N-glycans will be measure within two to three weeks post-surgery resection of the tumors because exosomes have a short half-life in circulation.

Descriptive data using mean, median and standard deviation for categorical data will be reported. Plots, tables and histograms will be illustrated. The average amount (nanogram or microgram) of the serum exosome bound tumor associated complex N-glycans among all groups and between any two groups will be compared using ANOVA and two-sample student t test. The differences at P<0.05 will be considered to be statistically significant. The diagnostic sensitivity (true-positive rate) and specificity (true-negative rate) will be evaluated and determined with the analyses of a Receiver Operating Characteristic (ROC) Curve. A new marker will be created by defining the optimal combinations of CA19-9 and the exosome bound tumor associated complex N-glycans detection by multiple methods: (1) the linear predictor from a multivariate logistic regression model including multiple markers; (2) the classification rule determined by classification tree; (3) linear combination of two or three of the markers that optimize the ROC curve. Optimal cutoff points will be obtained in a separate consideration to (1) maximize the Youden index (summation of sensitivity and specificity) for a maximum overall classification accuracy; (2) correspond to the perfect classification coordinate in the ROC curve, the (0,1) coordinate; (3) satisfy cost-benefit analysis; (4) satisfy a defined specificity while maximizing sensitivity. Corresponding to each optimal cutoff point, the diagnostic test statistical measures including sensitivity and specificity, positive and negative predictive values (PPV and NPV) will be derived. To compare between two markers, Delong's method will be conducted comparing the corresponding AUC or partial AUC estimates to compare the two markers. In the literature, CA19-9 alone was reported to have a sensitivity of ~0.74 and an AUC of 0.84 (variance=0.022) between pancreatic ductal adenocarcinoma (PDAC) and normal control. By our calculation, the sample size of 60 per group (normal, PDAC and cancer) will provide 80% power to compare the estimated AUC of 0.84 against the AUC of 0.5 of a random marker of no utility. The estimated AUC will be able to predict with a 95% confidence interval (0.797, 0.883). Note that statistical analysis is very important for developing cancer diagnostic assays.

Example 5. Additional Uses for the ExoELISA Assay

Additional studies include the following: (1). Screen pancreatic cancer high risk populations with the ExoELISA assay for early pancreatic cancer detection and diagnosis; the high risk populations include individuals with benign tumors of the pancreas (intraepithelial neoplasia, intraductal papillary mucinous neoplasms, and mucinous cystic neoplasms) and individuals with genetic conditions that predispose them to pancreatic cancer. (2). Compare the levels of the exosome bound tumor associated complex N-glycans between patients with operable and inoperable diseases to assess the value of measuring the exosome bound tumor associated complex N-glycans in estimation of pancreatic cancer clinical staging. The operable group will not include individuals with borderline resectable disease whose tumors become resectable after chemotherapy and/or radiotherapy. The inoperable group will include patients with locally advanced and metastatic disease. Favorable results from this study will help physicians to make treatment plans in the clinic. (3). Measure the serum exosome bound tumor associated complex N-glycans before and during therapeutic treatment to observe the response of tumors to chemotherapy and/or radiotherapy (i.e. correlate the levels of the exosome bound tumor associated complex N-glycans to tumor therapeutic response). (4). Evaluate the value of the serum exosome bound tumor associated complex N-glycans in monitoring disease progression and recurrence by measuring the serum antigen at different time points or regularly during the disease course. (5). Measure the exosome bound tumor associated complex N-glycansin other body fluids (urine and saliva) for pancreatic cancer early detection and diagnosis. (6). Count the number of circulating tumor associated complex N-glycan positive exosomes for early detection and diagnosis of pancreatic cancer, monitoring of tumor recurrence and response of tumor to therapeutics, and making treatment decisions (such as estimation of clinical staging and prediction of prognosis); this will be done using Exo-Flow methods (exosomes are first captured on larger magnetic beads, stained with antibody to the tumor associated complex N-glycans and secondary antibody conjugated with fluorescence dye, and then quantified using flow cytometric methods). (7). Study miRNA and other components contained in the tumor associated complex N-glycan positive exosomes in pancreatic cancer detection and diagnosis. (8). Expand the pancreatic cancer study to other types of tumors—colon rectal, lung, stomach and ovarian cancers. (9), Identify tumor associated complex N-glycan-presenting proteins or lipids to deepen understanding of the biological function of the tumor associated complex N-glycans in tumor initiation and development as well as progression; preliminary studies show multiple bonds with a molecular weight of above 60 on a Western blot after staining with mAb M9A12, indicating that multiple proteins or lipids could present the tumor associated complex N-glycans. (10) Detect and measure the exosome bound CA 19-9 in the serum of pancreatic cancer patients with the similar ExoELISA assay to see if it can improve tumor diagnostic sensitivity and specificity.

Example 6. ExoELISA Assay for Ovarian Cancer Detection and Diagnosis

At present, CA-125 is the best available marker for ovarian cancer detection and diagnosis. However, up to 20% of ovarian cancer (mainly mucinous carcinomas) lacks expression of CA125 antigen. Furthermore, CA-125 ELISA assay frequently used in the clinic misses 50 percent of early-stage (stage 1) ovarian cancer and has a significant false-positive rate in patients with benign diseases, such as diverticulitis, endometriosis, liver cirrhosis, pregnancy and uterine fibroids. Therefore, more sensitive and specific biomarkers and serum based assays for ovarian cancer are desperately needed.

In this study, the diagnostic value of the serum exosome bound tumor associated complex N-glycans for ovarian cancer was evaluated. Serum exosome bound tumor associated complex N-glycan amount in ovarian cancer group was compared to those of healthy controls and ovarian benign disease group. Next, the feasibility of measuring the serum exosome bound tumor associated complex N-glycans for early (stage 1) ovarian cancer detection and diagnosis was assessed. In ovarian cancer diagnosis, CA-125 test misses 50% of patients with early stage disease. Additionally, the possibility of measuring exosome bound tumor associated complex N-glycans in serum from patients with mucinous ovarian tumors was explored. CA-125 test is not suitable for patients with mucinous type of ovarian cancer because they lack CA-125 antigen expression.

Figure 1C:
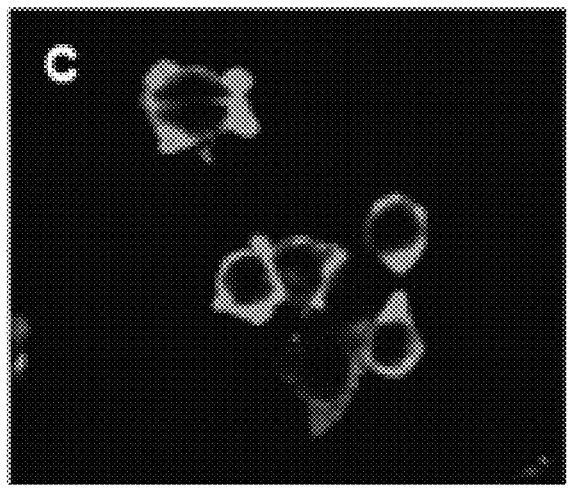
Figure 1D:
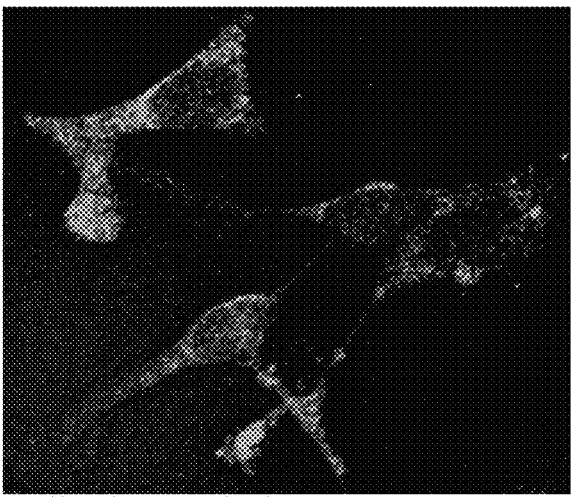

As demonstrated in FIG. 1A and FIG. 3, the novel tumor antigens, tumor associated complex N-glycans with terminal GlcNAcβ residues, were detected on the surfaces of ovarian cancer cells and mAb M9A12 intensively stained more than 80% of ovarian cancer tissues. Immunohistochemical staining of normal ovarian tissue, borderline cancerous tissue and cancerous tissue with mAb M9A12 was performed to identify specificity of mAb M9A12 in ovarian cancer (FIG. 10). Serous carcinomas (FIG. 10A, FIG. 10B) and mucinous carcinomas (FIG. 10C, FIG. 10D) stained intensely with mAb M9A12. The borderline tissue sample stained faintly with mAb M9A12 (FIG. 10E). Normal ovarian tissue did not appreciably stain with mAb M9A12. Most interestingly the exosome bound tumor associated complex N-glycans have been detected and quantitatively measured with elevated levels in serum from patients with ovarian cancer (FIG. 11).

Figure 13:
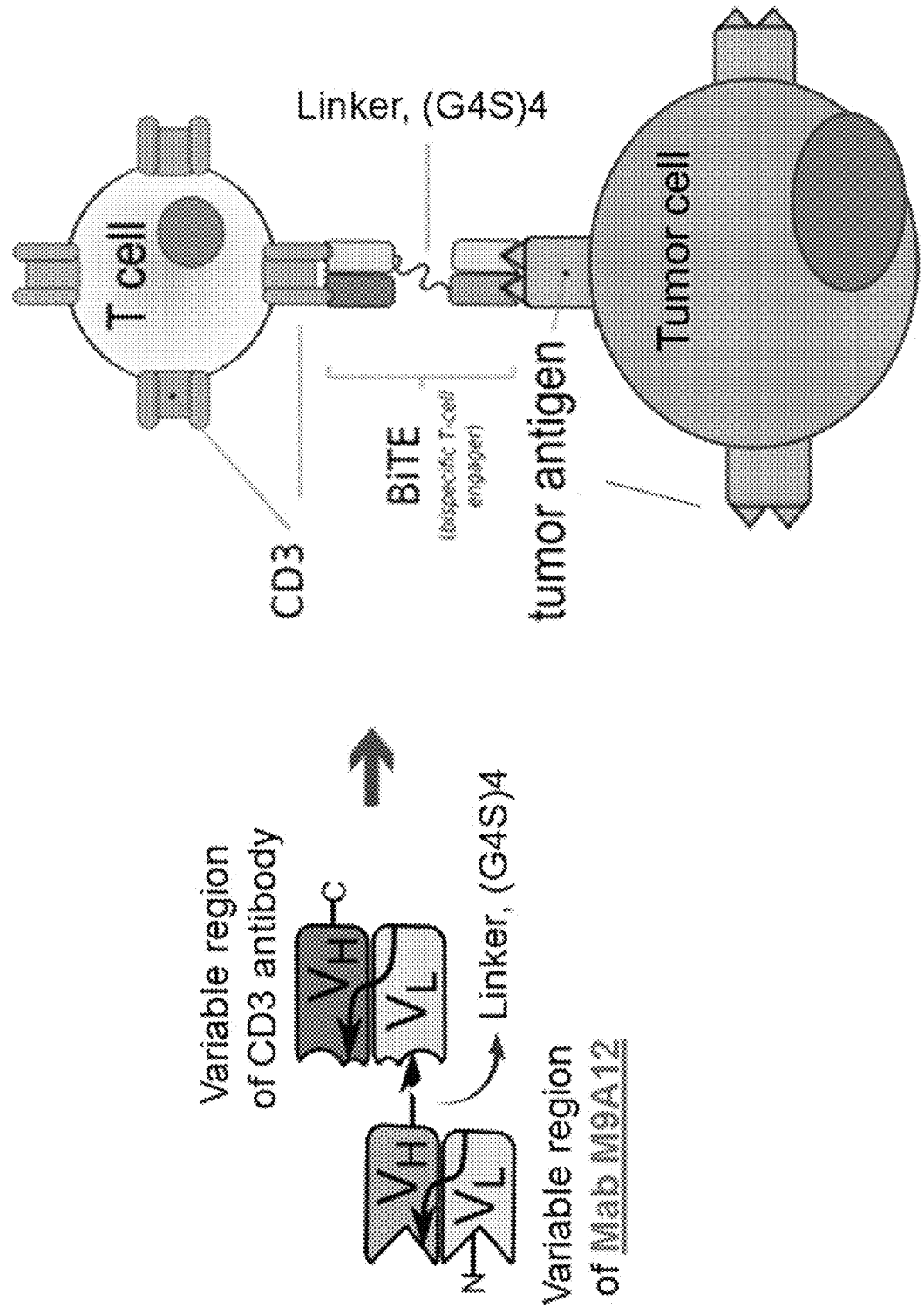
FIG. 13A depicts a schematic of a bi-specific T cell engager (BiTE) construct of mAb M9A12 and FIG. 13B depicts a schematic showing that the BiTE binds both T cells via CD3 (T cell membrane antigen) and tumor cells via tumor associated complex N-glycans with terminal GlcNAcβ residues.

Example 7. mAb M9A12 Constructs mAb M9A12 can be used to generate bispecific T cell engage (BiTE) antibodies. The variable region of mAb M9A12 can be conjugated to the variable region of a CD3 antibody via a linker (FIG. 13). The linker may be a $(G_4S)_4$ linker. Such an antibody binds to T-cells via the CD3 antibody and binds to tumor cells via the M9A12 antibody. This dual binding brings T cells in proximity to selectively attack tumor cells.

Figure 14:
FIG. 14 depicts a structure of a chimeric antigen receptor (CAR) with mAb M9A12 single-chain variable fragment (scFV). CD28 and 4-1BB are stimulatory ligands to enhance T-cell proliferation. CD3ζ is a T cell receptor.
Figure 15:
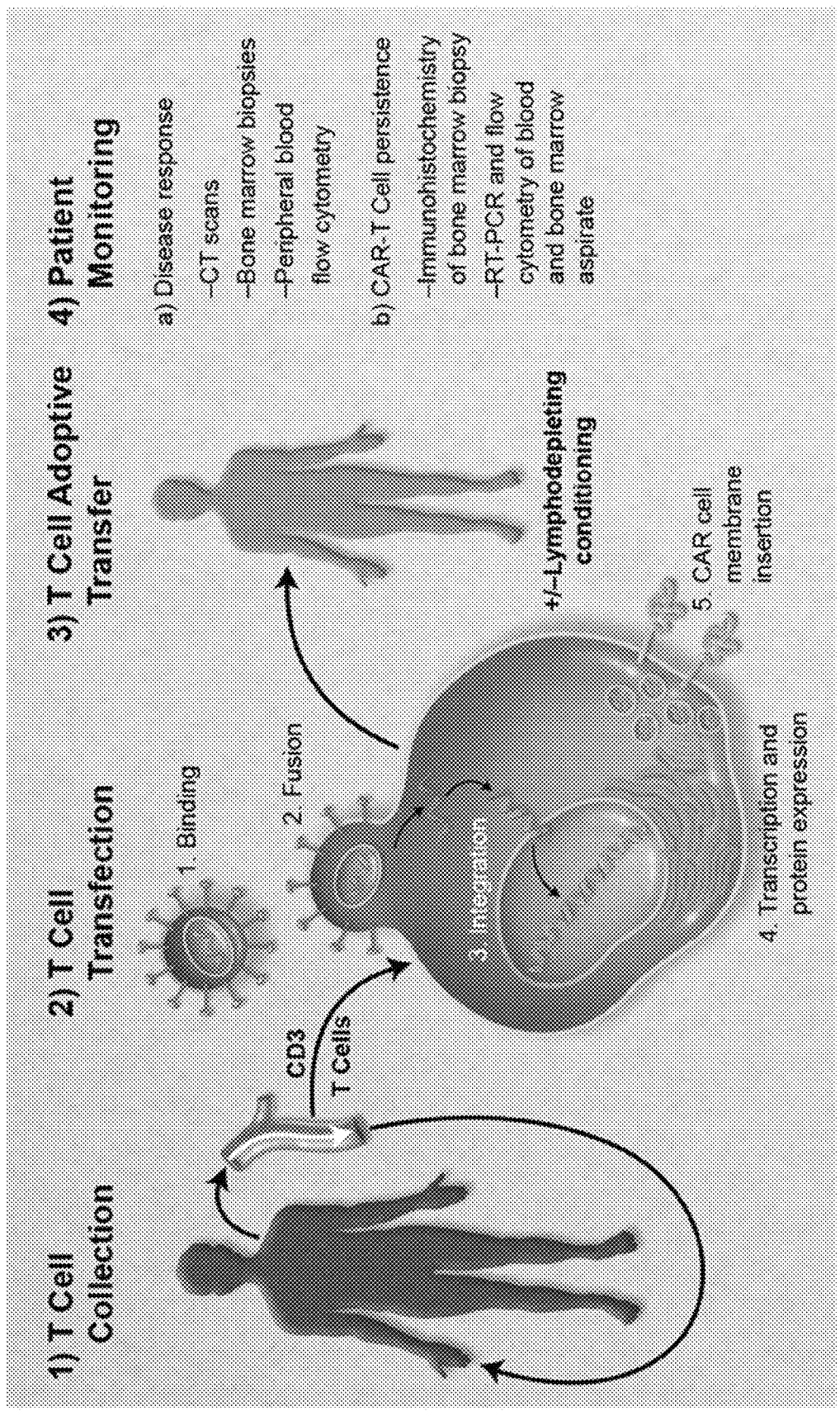
FIG. 15 depicts a schematic of adoptive cell transfer therapy with CAR-engineered T cells. The process starts with the binding of a CAR containing viral particle. Adapted from: en.wikipedia.org/wiki/Chimeric_antigen_receptor.

A chimeric antigen receptor (CAR) with mAb M9A12 may also be generated. Such a construct comprises mAb M9A12 single-chain variable fragment (scFv), stimulatory ligands to enhance T-cell proliferation and a T cell receptor (FIG. 14). The stimulatory ligands to enhance T-cell proliferation can be CD28 and 4-1BB. The T cell receptor can be CD3. Use of such a construct is depicted in FIG. 15 which shows adoptive cell transfer therapy with CAR-engineered T cells.

What is claimed is:

1. An isolated antibody, wherein the antibody comprises a light chain CDR1 comprising the amino acid sequence of SEQ ID NO: 1, a light chain CDR2 comprising the amino acid sequence of SEQ ID NO: 2, a light chain CDR3 comprising the amino acid sequence of SEQ ID NO:3, a heavy chain CDR1 comprising the amino acid sequence of SEQ ID NO: 4, a heavy chain CDR comprising the amino acid sequence of SEQ ID NO: 5, a heavy chain CDR3 comprising the amino acid sequence of SEQ ID NO: 6, and wherein the antibody specifically binds tumor associated complex N-glycans with terminal GlcNAcβ residues and recognizes an epitope within the tumor associated complex N-glycans.

2. The isolated antibody of claim 1, wherein the antibody comprises an amino acid sequence set forth in SEQ ID NO:8.

3. The isolated antibody of claim 1, wherein the antibody comprises an amino acid sequence set forth in SEQ ID NO:7.

4. The isolated antibody of claim 1, wherein the antibody is encoded by a nucleic acid sequence comprising a nucleic acid sequence selected from the group consisting of SEQ ID NO:9 and SEQ ID NO:10.

5. The isolated antibody of claim 1, wherein the antibody is selected from the group consisting of a single-chain antibody, an antibody fragment, a chimeric antibody, a humanized antibody, a bi-specific T cell engager (BiTE) antibody or a chimeric antigen receptor (CAR).

6. The isolated antibody of claim 5, wherein the antibody is a BiTE and further comprises an anti-CD3 scFv.

7. The isolated antibody of claim 5, wherein the antibody is a CAR and further comprises the intracellular domain from CD3-zeta (CD3).

8. The isolated antibody of claim 7, wherein the CAR further comprises CD28 and 41 BB.

9. The isolated antibody of claim 5, wherein the antibody conjugated to a payload selected from the group consisting of a therapeutic agent, a detectable, and a delivery device.

10. An immunoassay comprising at least one isolated antibody of claim 1.

11. A method for detecting a tumor in a subject, the method comprising:
    a) measuring an amount of tumor associated complex N-glycans with terminal GlcNAcβ residues in a biological sample obtained from a subject using at least one isolated antibody of claim 1; and
    b) comparing the amount of tumor associated complex N-glycans with terminal GlcNAcβ residues in the sample to a reference value, wherein a greater amount of tumor associated complex N-glycans with terminal GlcNAcβ residues in the sample compared to the reference value indicates the presence of a tumor in the subject.

12. The method of claim 11, wherein the biological sample is selected from the group consisting of blood, plasma, serum, saliva, sputum, ascites, tears, mucus of GI tracts, pleural effusion and urine.

13. The method of claim 11, further comprising isolating exosomes from the biological sample prior to measuring the amount of tumor associated complex N-glycans with terminal GlcNAcβ residues in the sample.

14. The method of claim 11, wherein the tumor is selected from the group consisting of pancreatic, ovarian, lung, stomach, colorectal, breast, prostate and esophageal and tongue/pharynx/larynx.

15. A method for monitoring response to treatment of a tumor in a subject, the method comprising:
    a) measuring an amount of tumor associated complex N-glycans with terminal GlcNAcβ residues in a biological sample obtained from a subject using at least one isolated antibody of claim 1;
    b) measuring the amount of tumor associated complex N-glycans with terminal GlcNAcβ residues in a second biological sample obtained from the subject after initiation of treatment using the at least one isolated antibody; and
    c) comparing the amount of the tumor associated complex N-glycans with terminal GlcNAcβ residues in the first sample to the amount of tumor associated complex N-glycans with terminal GlcNAcβ residues in the second sample, wherein a change in the amount of tumor associated complex N-glycans with terminal GlcNAcβ residues in the second sample as compared to the amount of tumor associated complex N-glycans with terminal GlcNAcβ residues in the first sample indicates a response to treatment.

16. The method of claim 14, wherein a decrease in the amount of tumor associated complex N-glycans with terminal GlcNAcβ residues indicates a decrease in tumor size and therefore tumor regression.

17. The method of claim 14, wherein an increase in the amount of tumor associated complex N-glycans with terminal GlcNAcβ residues indicates an increase in tumor size and therefore tumor progression.

18. The method of claim 14, wherein the biological sample is selected from the group consisting of blood, plasma, serum, saliva, sputum, ascites, pleural effusion and urine.

19. The method of claim 14, further comprising isolating exosomes from the biological sample prior to measuring the amount of tumor associated complex N-glycans with terminal GlcNAcβ residues in the sample.

20. The method of claim 14, wherein the tumor is selected from the group consisting of pancreatic, ovarian, lung, stomach, colorectal and esophageal and tongue/pharynx/larynx.

21. A method for detecting an early stage neoplasm in a subject, the method comprising:
    a) measuring an amount of exosome bound tumor associated complex N-glycans with terminal GlcNAcβ residues isolated from a biological sample obtained from a subject, the measuring step comprising using at least one isolated antibody of claim 1; and
    b) comparing the amount of exosome bound tumor associated complex N-glycans with terminal GlcNAcβ residues in the sample to a reference value, wherein a greater amount of tumor associated complex N-glycans with terminal GlcNAcβ residues in the sample compared to the reference value indicates the presence of a tumor in the subject.

* * * * *